United States Patent [19]

Sahmel et al.

[11] Patent Number: 4,459,227

[45] Date of Patent: Jul. 10, 1984

[54] PARA-HYDROXYPHENYLHYDRAZINES AS IN SITU PRECURSORS OF IMINOQUINONES AND QUINONES

[75] Inventors: Reinhardt O. Sahmel; Doyle G. Graham, both of Durham, N.C.

[73] Assignee: Duke University, Durham, N.C.

[21] Appl. No.: 239,625

[22] Filed: Mar. 2, 1981

[51] Int. Cl.³ .................. C07C 103/52; C07C 101/00; C07G 11/00; C07F 9/02
[52] U.S. Cl. ............................ 260/112.5 R; 564/310; 564/34; 260/923; 536/17.2; 536/17.5; 560/34
[58] Field of Search ...................... 260/112.5 R, 923; 564/310, 34; 536/17.2, 17.5; 560/34

[56] References Cited

U.S. PATENT DOCUMENTS

| | | | |
|---|---|---|---|
| 2,995,567 | 8/1961 | Sarett et al. | 260/319 |
| 3,419,659 | 12/1968 | Catino et al. | 424/60 |
| 3,884,919 | 5/1975 | Birchall et al. | 260/256.4 Q |
| 3,931,222 | 1/1976 | Cross et al. | 260/315 |
| 4,207,338 | 6/1980 | Eckhardt et al. | 424/309 |

OTHER PUBLICATIONS

Chem. Abstr., vol. 31, p. 4764.
Chem. Abstr., (1941), p. 6054.
Chem. Abstr., vol. 15, p. 7562.
Chem. Abstr., p. 8651.

Primary Examiner—Delbert R. Phillips
Attorney, Agent, or Firm—Oblon, Fisher, Spivak, McClelland & Maier

[57] ABSTRACT

Iminoquinone precursors having the formula

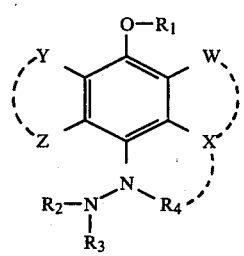

wherein $R_1$ represents hydrogen or an enzymatically hydrolyzable group; $R_2$ and $R_3$ independently represent hydrogen, a non-electron-withdrawing organic substituent or an enzymatically hydrolyzable group except that when $R_1$ is hydrogen, $R_2$ must be an enzymatically hydrolyzable group and $R_3$ must not inhibit the hydrolysis of $R_2$; $R_4$ represents hydrogen or an electron-withdrawing or non-electron-withdrawing organic substituent, except that if $R_1$ is hydrogen, $R_4$ may not inhibit the hydrolysis of $R_2$; W, X, Y and Z independently represent hydrogen or an electron-withdrawing or non-electron-withdrawing organic substituent, or any one of X and W, Y and Z, or X and $R_4$ taken together represents a cyclic or heterocyclic ring having 5 to 6 ring atoms; and wherein said enzymatically hydrolyzable group is selected so that a hydrolysis product is biologically benign for the biological system in which said precursor is present is produced by hydrolysis of the hydrolyzable group. Also disclosed are methods of synthesis and methods of use of these compounds.

20 Claims, 13 Drawing Figures

SYNTHESIS OF CHP(OBz)OEt

PROPOSED SCHEME FOR THE ENZYMATIC GENERATION
OF REACTIVE QUINONES FROM AA-CHP

SYNTHESIS OF AA-CHPs

SYNTHESIS OF Leu-CHP-OEt (XV)

SYNTHESIS OF Boc-Leu-CHP-BSA AND Leu-CHP-BSA

SPECTROPHOTOMETRIC STUDIES OF THE HYDROLYSIS OF LEU-CHP BY LAP

THE ULTRAVIOLET AND VISIBLE SPECTRUM OF CHP-OEt
AT pH 9.0 (A) AND pH 7.0 (B) AS A FUNCTION OF TIME

ULTRAVIOLET AND VISIBLE SPECTRA OF CHP-OEt IN THE PRESENCE OF $NaBH_4$(A), LYSINE(B) AND 3-MPA(C)

Figure 10:
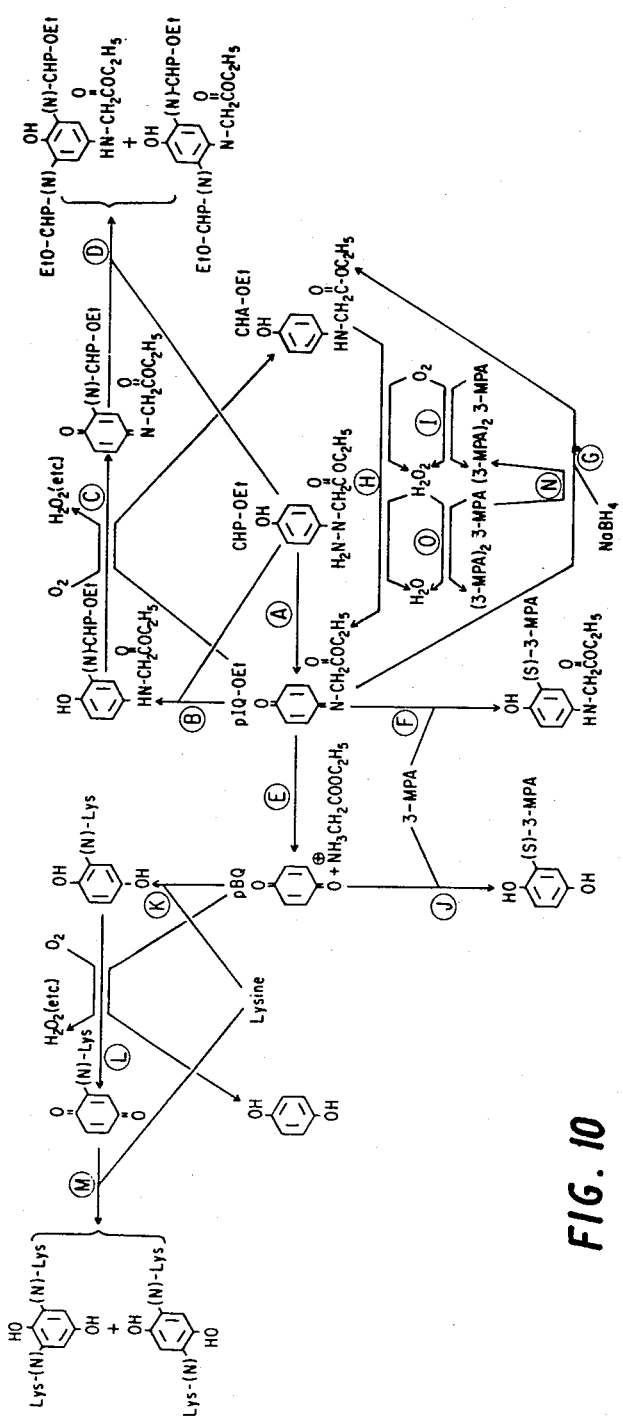

FIG. 10 PROPOSED SCHEME FOR THE REARRANGEMENT OF CHP-OEt AND RELATED COMPOUNDS

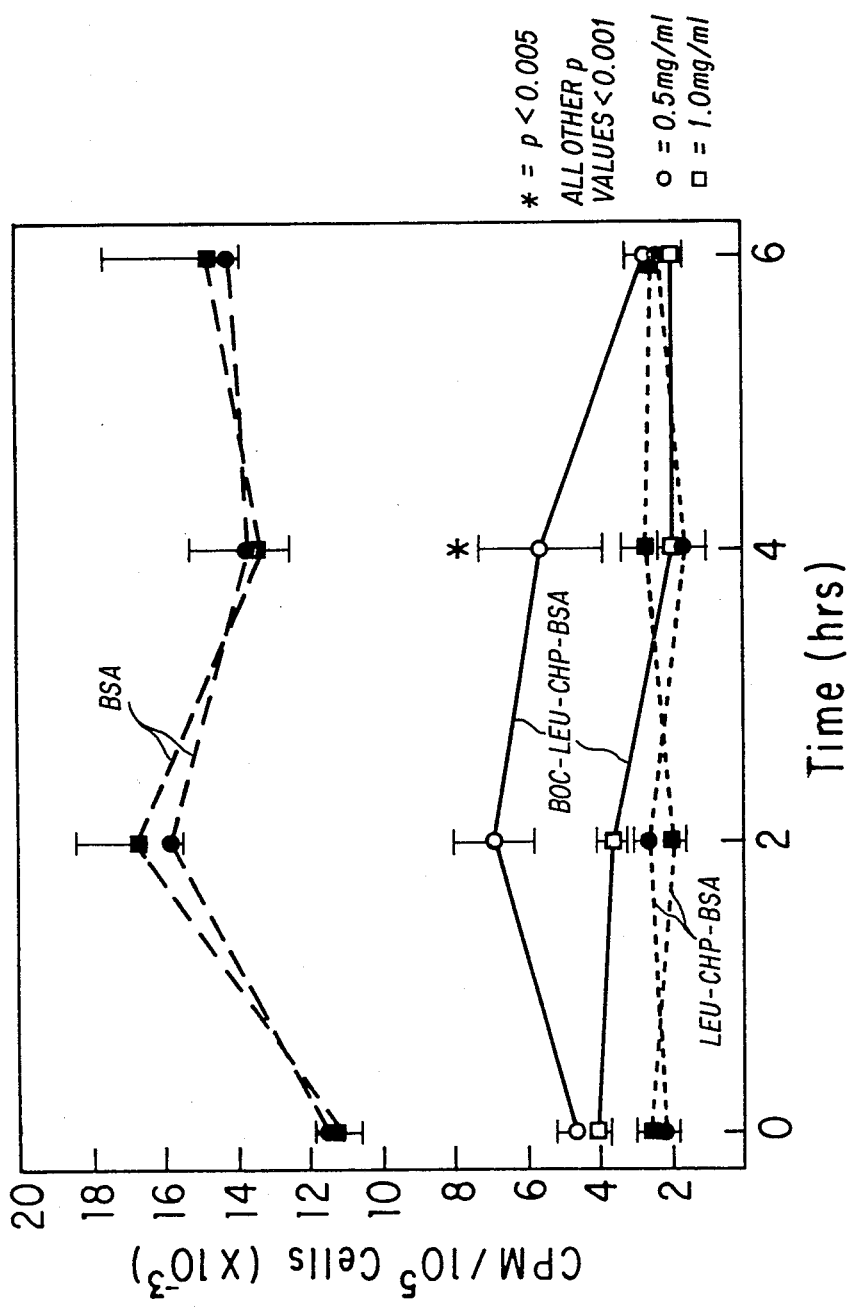

PARA-HYDROXYPHENYLHYDRAZINES AS IN SITU PRECURSORS OF IMINOQUINONES AND QUINONES

BACKGROUND OF THE INVENTION

1. Field of the Invention

This invention relates to precursors which will undergo elimination reactions to produce iminoquinones and quinones in situ after cleavage of a blocking group, and more particularly to para-hydroxyphenylhydrazine and its derivatives and their use as in situ precursors of iminoquinones and quinones.

2. Description of the Prior Art

Quinones and iminoquinones have many uses in biological systems as a result of their toxicity. The simplest quinone, p-benzoquinone, for example, was shown to be a potent bactericidal substance against *Salmonella typhosa* as early as 1911. Many other quinones and iminoquinones are also known to have biological activity. For example, chloranil (2,3,5,6-tetrachloro-1,4-benzoquinone) has marked antifungal properties, while blue-green algae are inhibited by 2,3-dichloro-1,4-naphthoquinone. When used in this application, the term "quinones" will refer generically to all the quinones whatever the number of rings on the substituents and the term "iminoquinones" will similarly refer to all iminoquinones, unless otherwise specified.

Nitrogen analogues of the quinones (i.e., iminoquinones) have not been as extensively studied as the quinones themselves, perhaps because iminoquinones hydrolyze rapidly in aqueous solutions to the corresponding quinones. Thus, they have been difficult to study in biological systems because of the uncertainty as to what the reactive species is, a quinone or an iminoquinone. This may not be important in biological systems since iminoquinones appear to exhibit roughly similar reactivity to quinones in the typical reactions that both undergo (both act as oxidizing agents and electrophiles). Iminoquinones have been prepared and tested for biological activity, for example in Hodnett et al, J. Med. Chem. 21, 11-16 (1978) which is hereby incorporated by reference, and have been shown to exhibit cytotoxic activity.

The toxicity of quinones and iminoquinones, and hence their biological activity, is caused by their high degree of reactivity, particularly with nucleophiles, such as the —SH group of cysteine and other biological thiols. However, this very reactivity works against them since they often react with other nucleophiles before reaching the site in the biological system where their activity is desired.

Accordingly, there have been attempts to use precursors of quinones and iminoquinones in order to produce the reactive compounds in situ. For example, p-benzohydroquinone has been used to generate p-benzoquinone in situ to prevent phage (viral) infections from proliferating in tissue cultures. However, this oxidation reaction to form the quinone is itself not very selective for biological systems, since oxidation can occur on standing in air. More desirable would be a precursor which forms the reactive quinone or iminoquinone selectively at a site of biological activity, e.g., an enzyme active site. In such a case the quinone would be generated only at sites of biological activity where reaction was desired. Although quinones and some iminoquinones have been extensively studied and reviewed, for example in J. L. Webb, "Enzyme and Metabolic Inhibitors", V.III, Academic Press, New York and London (1966), pp. 421-594, which is hereby incorporated by reference, no such precursors of general utility have previously been known.

There is however, a known reaction in which an iminoquinone is generated in situ in a biological system, although it represents only a minor side reaction rather than a general case. Researchers investigating the toxicity of N-(4-hydroxyphenyl)acetamide, also known as acetaminophen, discovered that about 2% of the acetaminophen was oxidized in liver cells (hepatocytes) to an N-hydroxylated compound that could lose a water molecule to form N-acetyl-p-iminobenzoquinone.

REACTION SCHEME I

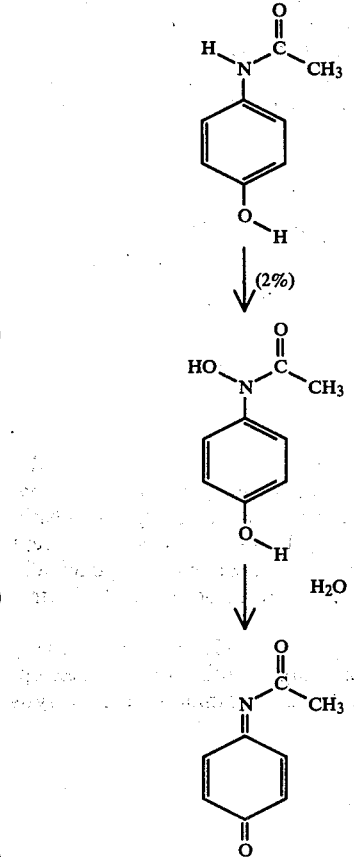

This iminoquinone was shown to be responsible for the toxic effects in the liver (1. Gillette, J. R. et. al.: "Biochemical Mechanism of Drug Toxicity" in Ann. Rev. of Pharmacology. 14:271 (1974) 2. Mitchell, J. R. et. al.: Handb. Exp. Pharmacol. 28/3 (1975) p. 383. 3. Potter, W. J. et al.: Pharmacology 12:129 (1974)).

Other investigators showed that by replacing the hydrogen of the phenolic hydroxyl group with a sulfate that could later be enzymatically cleaved, the intermediate N-hydroxylated amide could be isolated and studied (Gemborys, M. W. et al.: J. Med. Chem. 21:649-652 (1978)).

However, this reaction sequence does not provide a general method of producing quinones or iminoquinones in situ in other biological systems since it requires an initial oxidation by hepatocytes.

SUMMARY OF THE INVENTION

It is therefore an object of this invention to provide a method of introducing quinones or iminoquinones into a biological system without their being subjected to reactions before they reach the desired site of reactivity.

It is a further object of this invention to provide a method of generating quinones and iminoquinones in situ in biological systems.

It is yet another object of this invention to provide a precursor of quinones and iminoquinones that can be selectively de-blocked by the enzymatic systems of a biological organism to release a compound that will spontaneously form a toxic quinone or iminoquinone within the cell.

It is a still further object of this invention to provide blocking groups and precursors having structures that facilitate transport into the cells of the target organism.

These and other objects of this invention which will hereinafter become more readily apparent have been attained by providing precursors of iminoquinones having the formula

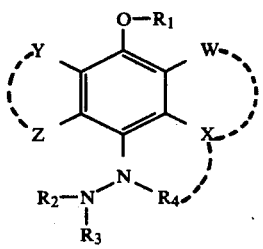

wherein $R_1$ represents hydrogen or an enzymatically hydrolyzable group; $R_2$ and $R_3$ independently represent hydrogen, a non-electron-withdrawing organic substituent, or an enzymatically hydrolyzable group except that when $R_1$ is hydrogen, $R_2$ must be an enzymatically hydrolyzable group and $R_3$ must not inhibit the hydrolysis of $R_2$;

$R_4$ represents hydrogen or an electron-withdrawing or non-electron-withdrawing organic substituent except that if $R_1$ is hydrogen, $R_4$ must not inhibit the hydrolysis of $R_2$;

W, X, Y and Z independantly represent hydrogen, or an electron-withdrawing or non-electron-withdrawing organic substituent, or any one of X and W, Y and Z, or X and $R_4$ taken together represents a cyclic or heterocyclic ring having 5 to 6 ring atoms; and O represents Oxygen and —NH—; and wherein said enzymatically hydrolyzable groups are selected so that hydrolysis products that are biologically benign for the biological system in which said precursor is present are produced by hydrolysis.

By a group that inhibits the hydrolysis of $R_2$ is meant any substituent that prevents the enzymatic hydrolysis of $R_2$ from occurring. An example, not intended to be limiting, is where $R_1$=H, $R_2$=Leucyl, and $R_3$=—CH$_3$. The methyl group inhibits the hydrolysis of the Leucylhydrazide bond. Other examples are well known in the art of enzyme biochemistry and can easily be determined using well-known methods for the study of enzymatic reactions.

By electron-withdrawing organic substituent is meant an organic substituent having a bond between the substituent and the atom to which it is attached in which the electrons are polarized toward the substituent more than they would be if the substituent was replaced with a hydrogen. A non-electron-withdrawing organic substituent is one in which either the electrons are polarized away from the substituent relative to the polarization that exists when a hydrogen is present or no difference in polarization exists. By biologically benign is meant not only products that do no harm to the individual cell in which hydrolysis takes place, but also those products that harm the cells in which the hydrolysis takes place but do not do major harm to other cells in the biological system to which the iminoquinone precursor has been administered.

Compounds having formula I have at least one blocking group that is hydrolyzable by an enzyme in a living organism. While the blocking group is present, no rearrangement or elimination reactions to form iminoquinones, and later to form quinones, is possible. However, once the blocking groups are removed, a spontaneous elimination of ammonia takes place to give an iminoquinone. This reaction can be catalyzed by either acid or base and is shown in Scheme II, where $R_2$, $R_3$ and $R_4$ have the same meanings given above where $R_1$=H, and W, X, Y and Z have the same meanings given above:

Reaction Scheme II

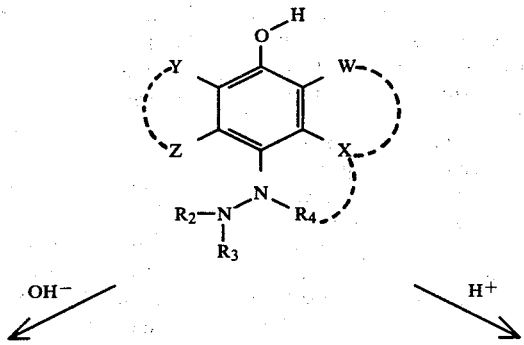

-continued
Reaction Scheme II

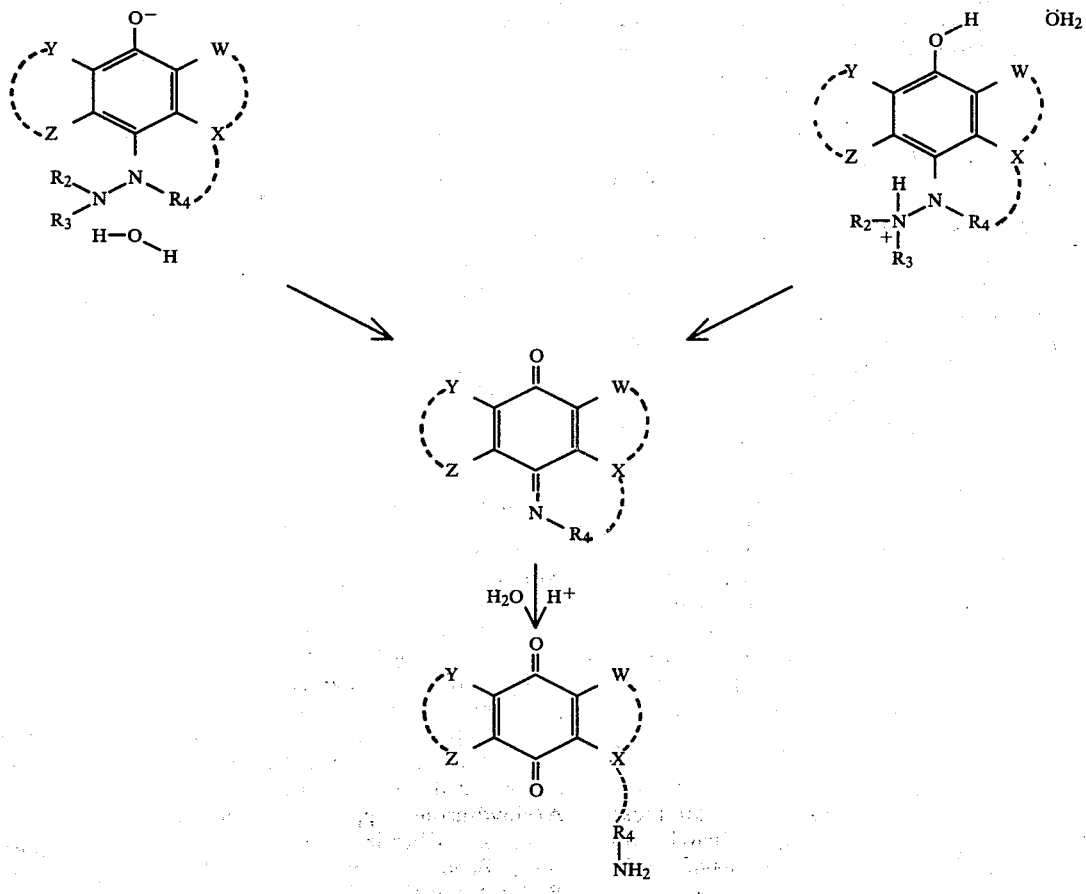

As can be seen in Scheme II, further reaction to give a quinone may also take place.

As indicated above, these rearrangements are prevented from occurring prematurely by providing a blocking group on the β-nitrogen or phenolic oxygen. By chosing a blocking group that is hydrolyzable by an enzymatic system, release of the compound capable of ammonia elimination does not occur until the precursor is present in the desired biological system. In fact, the precursor can be easily designed for hydrolysis by a particular enzyme or class of enzymes.

Any blocking group that is hydrolyzable by an enzyme is suitable for the compounds of the present invention, within the limitations discussed herein. Examples of classes of enzymes present in biological systems include carboxylic acid hydrolases, phosphoric monoester hydrolases, phosphoric diester hydrolases, sulfuric ester hydrolases, glycoside hydrolases, N-glycosyl hydrolases, peptide hydrolases, α-amino-acyl-peptide hydrolases, peptidyl-amino-acid hydrolases, dipeptide hydrolases, peptidyl-peptide hydrolases, and any other hydrolytic enzyme present in biological systems.

The suitability of a particular blocking group for hydrolysis by a specific enzyme system can be easily determined by simple experimentation since the blocked precursor compound, being derivative of phenylhydrazine, will have a greatly different visible/ultraviolet absorption spectra from the iminoquinone and quinones that will be produced by spontaneous reactions upon deblocking in aqueous solutions, as is well known in the art.

Blocking groups suitable for the phenolic oxygen include phosphate, pyrophosphate, glycosyl, ribosyl, deoxyribosyl, acyl, arylacyl, aminoacyl, peptidyl and sulfate. Each of these groups is cleavable by a particular class of hydrolase, e.g., phosphate by phosphatases, pyrophosphate by pyrophasphatases, glycosyl by glycoside hydrolases, ribosyl by riboside hydrolases, deoxyribosyl by deoxyriboside hydrolases, acyl and arylacyl by carboxylic ester hydrolases, aminoacyl and peptidyl by peptide hydrolases, and sulfate by sulfuric ester hydrolases. There is no particular limit to the nature of the individual types of blocking groups, except that the corresponding hydrolysis reaction should not be impaired severely. This is easily determined by simple experimentation, as has been discussed above. Preferred glycosyl blocking groups are prepared from $C_5$ or $C_6$ naturally occurring glycosides. Preferred aminoacyl groups are α-amino acids, while preferred acyl or arylacyl groups have 2–30 carbons. Most preferred are compounds in which $R_1$=H and $R_2$ acts as the blocking group.

Substituents $R_2$ and $R_3$ are not required to be enzymatically hydrolyzable if $R_1$ is an enzymatically hydrolyzable group. When $R_1$ is hydrolyzable, $R_2$ may be hydrogen, alkyl, aryl, or arylalkyl and $R_3$ may be hydrogen or alkyl. $R_2$ may at any time be a hydrolyzable group such as aminoacyl, peptidyl, glycosyl, ribosyl, deoxyribosyl, acyl, arylacyl, or phosphate. When $R_2$ is one of the hydrolyzable groups listed herein, $R_3$ must not inhibit the hydrolysis of $R_2$.

Substituent $R_3$ may be hydrogen or an alkyl group except that when $R_2$ is a hydrolyzable group, $R_3$ must not inhibit the hydrolysis of $R_2$. When $R_3$ is an alkyl group, 1-5 carbons are preferred and method is most preferred.

Substituent $R_4$ may be hydrogen, alkyl, aryl, acyl, arylacyl, aminoacyl, peptidyl, glycosyl, ribosyl, deoxyribosyl, phosphate, or halogen except that when $R_2$ is a hydrolyzable group, $R_4$ may not inhibit the hydrolysis of $R_2$. When $R_4$ is hydrolyzable, it is subject to the same conditions and limitations as discussed for $R_1$. Preferred alkyl groups are carboxyalkyl groups. Most preferred are (alkyl) carboxymethyl groups having an alkyl substitutent on the methyl carbon selected from the group consisting of side chains present in naturally occurring amino acids. Preferred aryl groups are those based on benzene and most preferred is phenyl. Preferred halogens are chlorine and bromine with chlorine most preferred.

W, X, Y and Z may independently represent hydrogen, halogen, hydroxyl, amine, alkoxy, alkyl, alkenyl, carboxyl, formyl, aryloxy, alkyl or dialkyl amine, thioalkyl, cyano, acyl amine, aryl, or arylalkyl. Preferred halogens are chlorine and bromine and most preferred is chlorine. Preferred alkoxy groups are those having 1–30 carbon atoms and most preferred are those having 1–12 carbon atoms. Preferred alkyl groups are those having 1–30 carbon atoms and most preferred are those having 1–12 carbon atoms. Preferred alkenyl groups are those having 1–30 carbon atoms and 1–10 double bonds while most preferred are those having 1–20 carbon atoms and 1–5 double bonds. Preferred aryloxy groups are those based on benzene and most preferred is phenyl. Preferred alkyl and dialkyl amines are those having 1–30 carbon atoms per alkyl group and most preferred are those having 1–12 carbon atoms per alkyl group. Preferred thioalkyl groups are those having the sulfur attached to the ring and 1–30 carbon atoms with 1–12 carbon atoms being most preferred. Preferred acylamines are those containing 1–30 carbon atoms or formed from a naturally occurring α aminoacid or peptide while most preferred are those containing 1–12 carbons. Preferred aryl groups are those based on benzene and most preferred is phenyl. Preferred arylalkyl groups are those having 1–20 carbons in an alkyl chain and an aryl group based on benzene while most preferred is benzyl.

Alternately, any one of X and W, Y and Z, or X and $R_4$ taken together may represent a cyclic or heterocyclic ring having 5 to 6 atoms when considered together with the atoms of the phenylhydrazine to which they are connected. Suitable heteroatoms include nitrogen, oxygen, and sulfur. The ring may additionally contain unsaturation in the form of carbon-carbon or carbon-nitrogen double bonds. Preferred for X and W or Y and Z are 6-membered aromatic rings such that the resulting structure is a naphthalene or anthracene derivative. Most preferred are naphthalene derivatives. Preferred for X and $R_4$ are 5- or 6-membered rings. Most preferred are 5- or 6-membered rings having the αnitrogen of the hydrazine functional group present as the only hetero atom.

The names of different types of substituents disclosed herein refer to the linkage of these substituents to the phenylhydrazine and are not intended to limit the occurrence of other functional groups within the substituent.

The compounds of the present invention may easily be synthesized by known methods of organic chemistry. Many synthetic methods are known for producing phenylhydrazines, the basic structural class to which the compounds of the present invention belong, for example, as disclosed in: Edgar Enders: Methoden Zur Herstellung und Umwandlung von Arylhydrazinen und Arylhydrazonen. pp 169–691 in Methoden der Organischen Chemie (Houben-Weyl), Eugen Muller (Ed.), Band X12, Stickstoff-Verbindungen I, Teil 2, Rudolf Stroh(Ed.). Georg Thieme Verlag (1967) Stuttgart. One easy method that exists for converting quinones having known toxicity and end uses into the compounds of the present invention is shown in Scheme III.

Reaction Scheme III

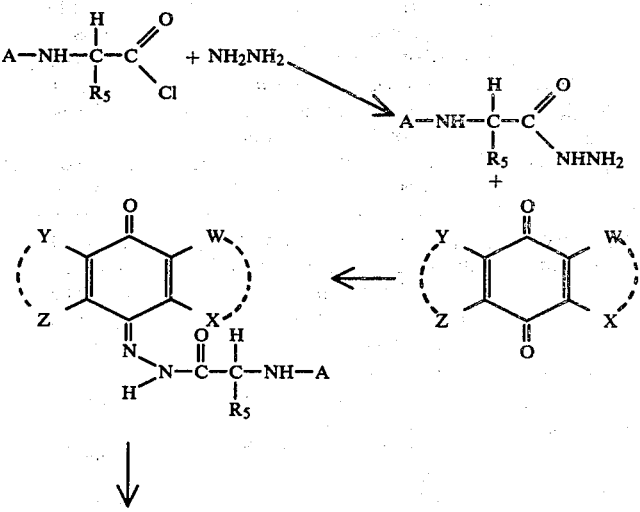

Reaction Scheme III

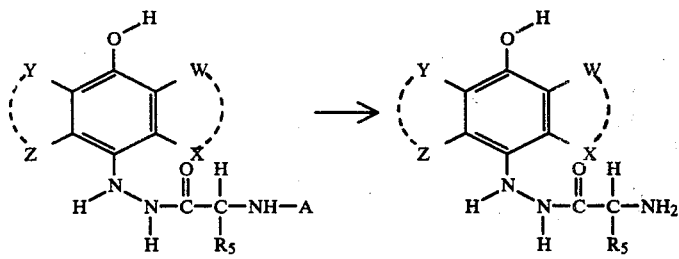

-continued

In this reaction, an βN-(amino acyl) phenyl hydrazine is prepared by reacting an aminoacyl chloride or anhydride having the αnitrogen and any other reactive groups on the side chain protected by a suitable blocking group, e.g., tert-butoxycarbonyl, with hydrazine. In these reactions, W, X, Y and Z have the meanings previously assigned, A is a protective group typically used in peptide synthesis (e.g. tert-butoxycarbonyl, and $R_5$ is selected from the group consisting of side chains present in naturally occurring amino acids. The resulting hydrazide is reacted with a quinone to give an iminoquinone that can be reduced with ascorbic acid or other mild reducing agents to the desired phenylhydrazine derivative. If desired, the protecting groups on the amino acid moiety may now be removed.

The βN-(aminoacyl)phenylhydrazine compounds produced in these reactions are compounds of the present invention. The aminoacyl blocking group is cleavable by aminopeptidases to give the phenylhydrazine derivative that is the immediate precursor of the iminoquinone (and quinone), as was shown in Reaction Scheme II. The quinone that is released as the final product of these reactions is the same quinone that was used in the synthesis of the β—N-(aminoacyl)phenylhydrazine. Accordingly, this synthetic pathway provides a simple way of converting quinones having a known end use as a toxic substance, e.g., fungicide, bactericide, etc., into a more stable precursor for ease of administration.

Many examples of such biologically active quinones, which could be used to synthesize the iminoquinone precursors of the present invention, are known, including ρ-Benzoquinone, Toluquinone, ρXyloquinone, Cumoquinone, Duroquinone, Thymoquinone, 5-Methoxy-toluquinone, Tetrachloroquinone (chloranil), 1,4-Naphthoquinone, Menadione, Phthiocol, Lawsone, Juglone, Naphthazarin, 2,3-Dichloro-1,4-naphthoquinone, Lapachol, Lomatiol, and 9,10-Anthraquinone.

One preferred form of the compounds of the invention are blocked αN-(carboxymethyl)-p-hydroxyphenylhydrazines or derivatives thereof. Such a compound is an aminoacid analogue per se and in its more preferred form uses a naturally occurring amino acid or another module of itself as a blocking group on the βnitrogen. The resulting compound is a peptide analogue, and thus suitable for any biological system containing peptidase enzymes. Compounds having the general formula

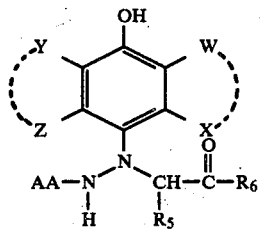

are compounds of this preferred type, where W, X, Y and Z have the meanings previously described, $R_5$ is selected form the group consisting of side chains present in naturally occurring amino acids, and $R_6$ is hydroxy, alkoxy, —O—M' where M' represents a singly charged metal ion, amino acid, or

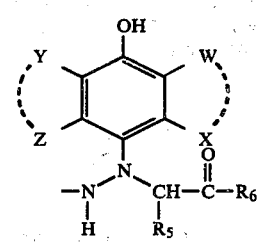

and AA is an αaminoacid, acyl, arylacyl, or phosphate. These compounds can be synthesized by known methods of organic synthesis, including the method outlined in Scheme IV below.

Reaction Scheme IV

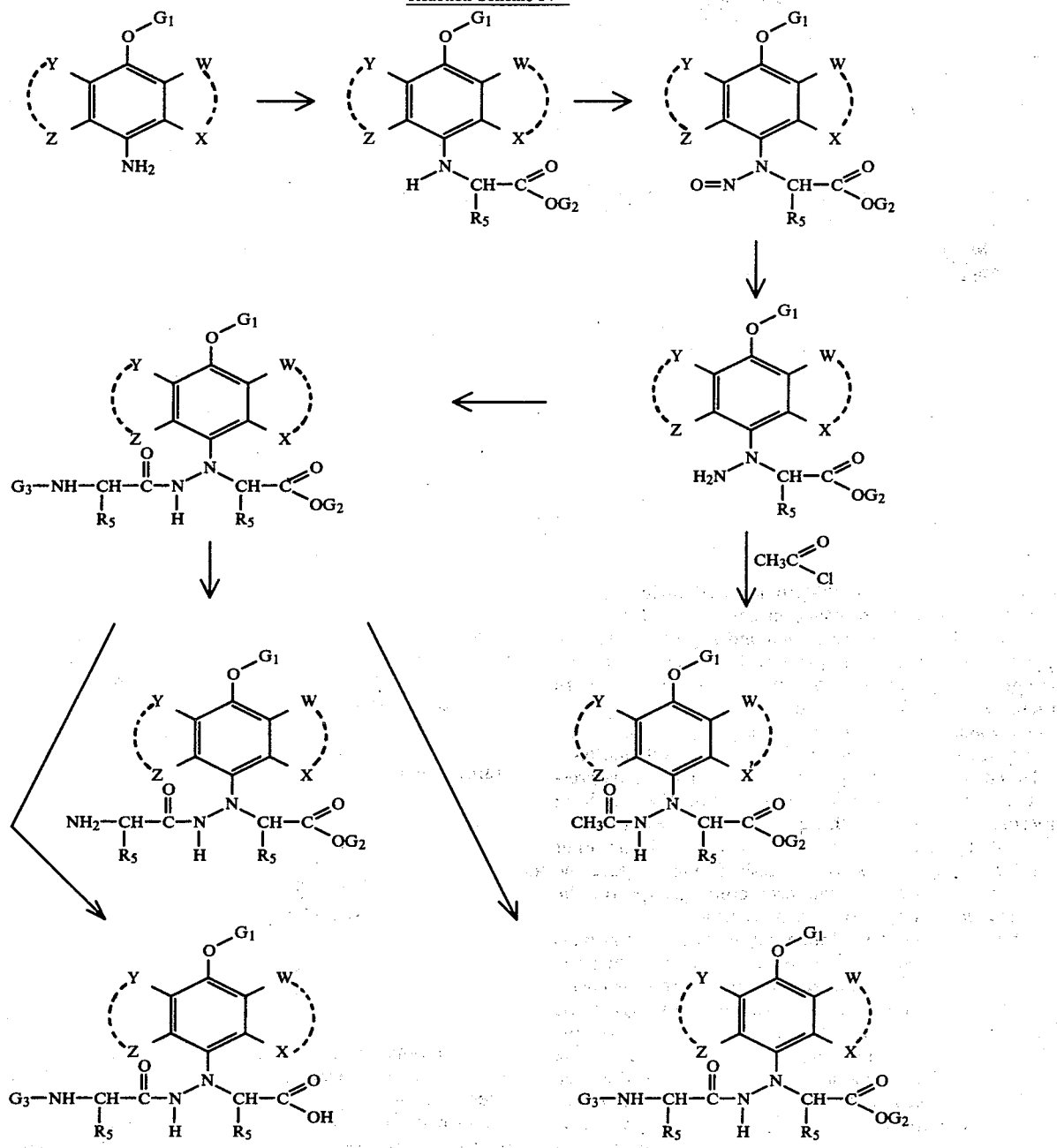

In this method a *p*hydroxyaniline having a protective group $G_1$, (typically benzyl) and having substituents W, X, Y and Z as previously defined, is reacted with a compound having the formula

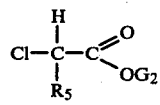

where Cl represents chlorine or bromine, $R_5$ is as previously defined, and $G_2$ is a protective group, typically a lower alkyl group such as methyl or ethyl. The resulting secondary amine is reacted in typical fashion with sodium nitrite in aqueous HCl or with nitrous acid generated in some other fashion to form a N-nitrosamine. The nitrosamine is reduced by any suitable method, typically with an aluminum amalgam, to form the hydrazine. The hydrazine is reacted with an aminoacid having a protecting group $G_3$ on the α-nitrogen and on any other basic nitrogens that are present. A typical protective group is Boc (tert-butoxycarbonyl). If the various protecting groups have been chosen so that each may be removed separately, as illustrted by the typical examples of protecting groups $G_1$–$G_3$ given above, individual protecting groups may be removed and additional reactions may occur at the de-protected positions to give further products of the invention, as illustrated in part by Reaction Scheme IV. These and the other embodiments of the invention are within the normal scope of manipulations commonly practiced by those skilled in the art to which this section of the invention pertains, organic chemistry, and particularly the chemistry of peptide synthesis.

Compounds of the present invention may be used as replacements for quinones and iminoquinones in any biological use that relies on the toxicity of these compounds. They have an advantage in that quinones and iminoquinones are generated spontaneously from them in situ after enzymatic cleavage of the blocking group. Thus, degradation or reaction cannot occur except in a biological system to which they are administered.

Compounds having a carboxymethylphenylhydrazine structure can be easily attached to a protein or polypeptide by known methods of attaching acyl-containing compounds to proteins. Preferred are naturally occurring or synthetic proteins and polypeptides have 1 to 500 functional groups that can be acylated. Coupling of pro-drugs to proteins and peptides is a method known to enhance cellular ingestion by pinocytosis and to reduce the toxic effects of the pro-drug prior to ingestion and release of the drug form itself. Bovine serum albumin is a typical naturally occurring protein that may be used in this fashion.

In order to better reach a location in which iminoquinone formation is desired, compounds of the invention may be administered in a pharmaceutical carrier chosen for the type of organism being treated. The resulting mixture may be a solution, suspension, cream salve, powder, or other physical form intended for use by injection, ingestion, or contact. Suitable carriers depend on the type of organism being treated and the desired physical characteristics of the resulting mixture and generally include water, alcohol, oils, dimethylsulfoxide, and other non-toxic solvents as well as talc and inert ingredients. In certain applications, e.g. killing algae in non-potable water, the restriction to non-toxic solvents may be removed. If desired other active ingredients may be combined with the compounds of this invention for ease of administration.

The compounds of this invention provide a convenient means by which iminoquinones can be formed in situ in a biological system. By biological system is meant either intracellularly in a single- or multi-cellular organism or in a fluid containing biological products of such cells that is in contact with the cells. By proper choice of blocking groups so that the compounds are prepared for a specific enzyme or transport system, selective formation of the iminoquinone, and hence the quinone, can occur in one cell or tissue in the presence of a second cell or tissue. By selective formation is meant formation either more rapidly or in a higher concentration for whatever reason. Selective formation is likely to be caused by differences in the amount of targeted enzyme in different cell or tissue types.

An additional advantage of the present invention over direct use of the quinones themselves is that the enzymatically hydrolyzable blocking groups of the present invention also should participate in transport systems that move substrates into cells. Mediated and active transport of many biological substrates, such as glycosides, ribosides, and peptides, is well documented. Since the compounds of the present invention are all substrates for an enzyme reaction that can occur in the interior of a cell, they should all be transportable, to at least some extent, by the same transport systems that convey the normal substrates for the enzymes.

It is anticipated that the compounds of the present invention will find use as in multicelluluar organisms. They are most active in cells having the highest hydrolytic activity for the enzymatically hydrolyzable blocking group present on a particular compound. By routine design and experimental choices of a blocking group or groups, it will be possible to produce quinones and iminoquinones in selected cells or tissues of a multicellular organism. Compounds of the invention have been shown to be substrates of leucine aminopeptidase (LAP), an enzyme known to be present in leukemia cells, and to inhibit the synthesis of DNA of these cells. The inhibition of DNA synthesis by quinones is known. In vitro hydrolysis of $\beta$N-(L-leucyl)-$\alpha$N-(carboxymethyl)-p-hydroxy-phenylhydrazine (Leu-CHP) and several other compounds of the invention by LAP has been demonstrated. The ultimate elimination products of iminoquinones and p-benzoquinone have been demonstrated in this in vitro experiment and in an in vivo experiment in which the quinone and iminoquinones were generated in situ in L1210 murine leukemia cells. Thus, the original hypothesis of in situ quinone production has been proven. However, an attempt to prolong the life of mice infected with leukemia using compounds of the invention was not effective, apparently due to a poor choice of blocking group resulting in low solubility and rapid clearing by the kidneys. Nevertheless, choice of proper blocking groups and quinoidal structures is well within the routine experimentation commonly practical in pharmacology, now that the general principles and specific examples of the present invention have been disclosed.

The above disclosure generally describes the present invention. A more complete understanding can be obtained by reference to the following specific examples, which are provided herein for purposes of illustration only and are not intended to be limiting unless otherwise specified.

Figure 1:
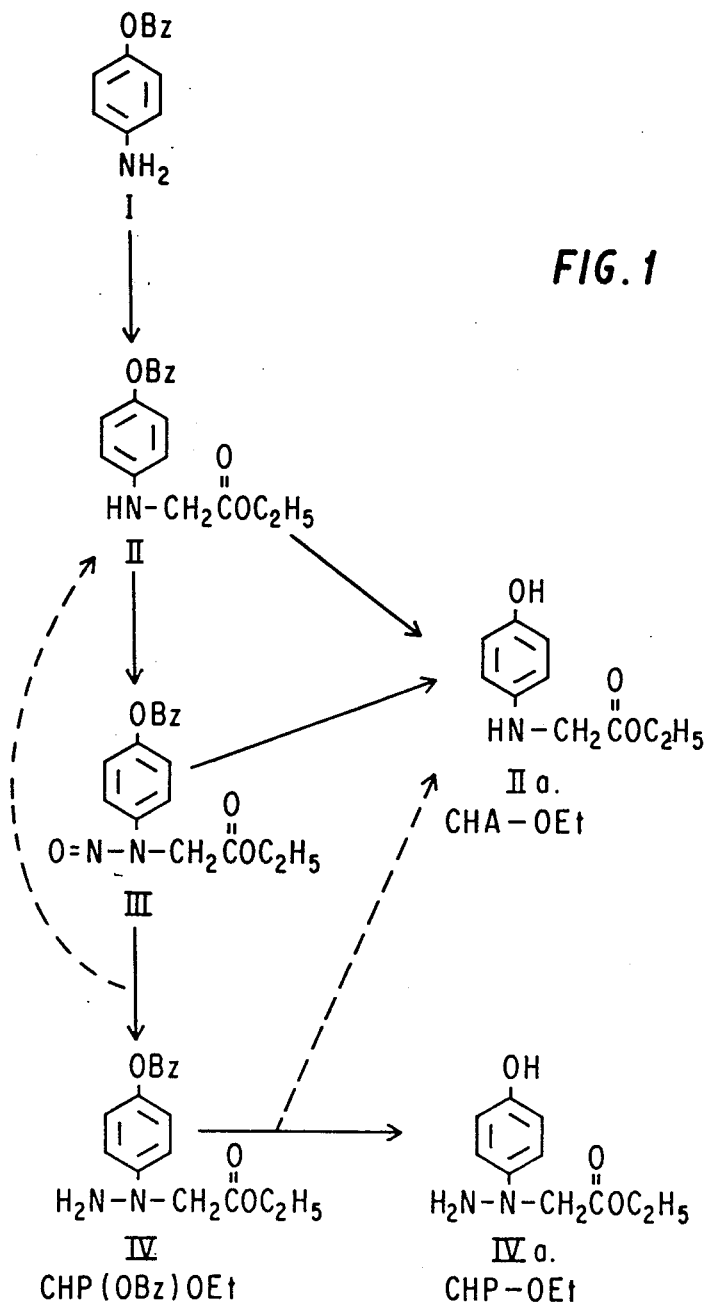

EXAMPLE 1 (See FIG. 1)

The free base of p-benzyloxyaniline (I) was obtained by extraction of the hydrochloride from 1N NaOH into diethyl ether ($Et_2O$). The $Et_2O$ solution was separated, dried over $Na_2SO_4$, filtered and rotoevaporated down to a beige prismatic solid. I (79.0 gm, 0.397 mole), ethylchloroacetate (57.5 gm, 0.47 mole), and dry triethylamine (TEA) (47.5 gm, 0.47 mole) were added to absolute ethanol (EtOH)(300 ml) and refluxed under nitrogen ($N_2$) in a 1000 ml, three-necked, round bottom flask (3N-RBF) fitted with an overhead mechanical stirrer (OMS) and water-jacketed condenser. After 48 hours, the reaction was cooled to room temperature and to it was then added $Et_2O$ (700 ml) and the resulting TEA-HCl precipitate was filtered off. The solution was extracted with 0.2N HCl, 0.2N NaOH and finally $H_2O$ and the organic layer was separated, dried over $Na_2SO_4$, filtered and rotoevaporated down to a light brown prismatic solid (II). Yield: 91 gm (80% theoretical).

In an ice bath cooled 1000 ml 3N-RBF fitted with an OMS, II (35 gm, 0.122 mole) was added to a solution of concentrated HCl (20 ml) and ice (70 ml). To this a solution of $NaNO_2$ (9.5 gm) in $H_2O$ (30 ml) was added dropwise and allowed to react at 4° C. for 2–3 hours. $Et_2O$ (500 ml) was then added directly to the reaction mixture and the product was extracted into the $Et_2O$. This was then extracted with 0.2N NaOH, then $H_2O$, dried over $Na_2SO_4$, filtered and rotoevaporated to yield a white solid. This was washed with petroleum ether and filter dried. Yield: 26.4 gm (68.5%).

In order to provide N(p-hydroxyphenyl)glycine ethyl ester for later comparisons, II (2.85 gm, 0.01 mole) was dissolved into 15-20 ml of dioxane, palladium on carbon catalyst (Pd/C)(150 mg) was added while $N_2$ was bubbled through the solution and the suspension was then catalytically hydrogenated (45-50 psi $H_2$) for about 2 hours. The catalyst was filtered off and the solvent rotoevaporated to a light yellow liquid which was dried on the high vacuum pump for a few hours and allowed to stand at room temperature overnight. The next day the oil had crystallized into yellow needles which were washed with petroleum ether and filter dried. The structure was confirmed by NMR. Yield: 1.85 gm (95%).

Synthesis of α-N-(carboxymethyl ethyl ester)-p-benzyloxphenylhydrazine (CHP(OBz)OEt)(IV).

In an ice bath cooled 1000 ml 3N-RBF fitted with an OMS, ethyl acetate (EtOAc)(300 ml), EtOH (50 ml) and $H_2O$ (25 ml) were mixed. Freshly prepared aluminum amalgam (Al(Hg)) was added by taking cut up aluminum (6 gm) and exposing it to 0.1N NaOH until gas evolution was rapid. The water was decanted, the foil was washed briefly with tap water, decanted again and enough 2% $HgCl_2$ solution added to cover the Al. After about 2 minutes, the gray solution was decanted and the Al(Hg) was washed successively with $H_2O$, EtOH and EtOAc. After the EtOAc was decanted, the Al(Hg) was added directly to the solution containing III. A second batch of Al(Hg) was prepared in an identical fashion and also added to the reaction vessel. The reduction was complete after 2 hours as judged by silica gel thin layer chromatography (SG-TLC). The major product was the desired IV while the minor product was regenerated II. The unreacted Al(Hg) was first filtered off and washed with EtOAc using a Buchner funnel without filter paper. The filtrate was then refiltered and the clear filtrate was dried over $Na_2SO_4$. This was filtered off and the filtrate was rotoevaporated to yield a white prismatic solid which was washed with petroleum ether and filter dried. Yield: 17.4 gm. To remove II (as the impurity), the solid was taken up in 100 ml of hot EtOH and recrystallized. After at least 8 hours, the solid IV was filtered off, washed with petroleum ether and filter dried. Yield: 14.6 gm (71%).

EXAMPLE 2 (See FIG. 1)

Synthesis of α-N-(carboxymethyl ethyl ester)-p-hydroxyphenylhydrazine CHP(OEt) (IVa)

All preparations of IVa were done the same day experiments were to be performed using it. IV (2.0 gm), (0.0067 mole) was dissolved in dry THF and hydrogenated for 2 hours. (45-50 psi $H_2$) in the presence of Pd/C. The catalyst was filtered off and the THF was rotoevaporated off leaving a clear light yellow oil behind. (The analysis reveals a mixture of IIa and IVa.) $Et_2O$ (20-30 ml) was added to this and the solution (10 ml) was preparatively chromatographed on thick SG-TLC plates with fluorescent indicator using an anhydrous $Et_2O$/Pet ether (2:1) solvent system. Each plate was developed twice. The desired product (IVa) ($R_f$=0.05) was obtained after scraping off the silica gel, stirring thoroughly in anhydrous $Et_2O$, filtering off the silica gel and rotoevaporating off the $Et_2O$. The light yellow oil was dried for 2 hours with a high vacuum pump down to a colorless oil which was further dried on the high vacuum pump overnight. This product was used in subsequent in vitro and in vivo experiments.

Figure 3:
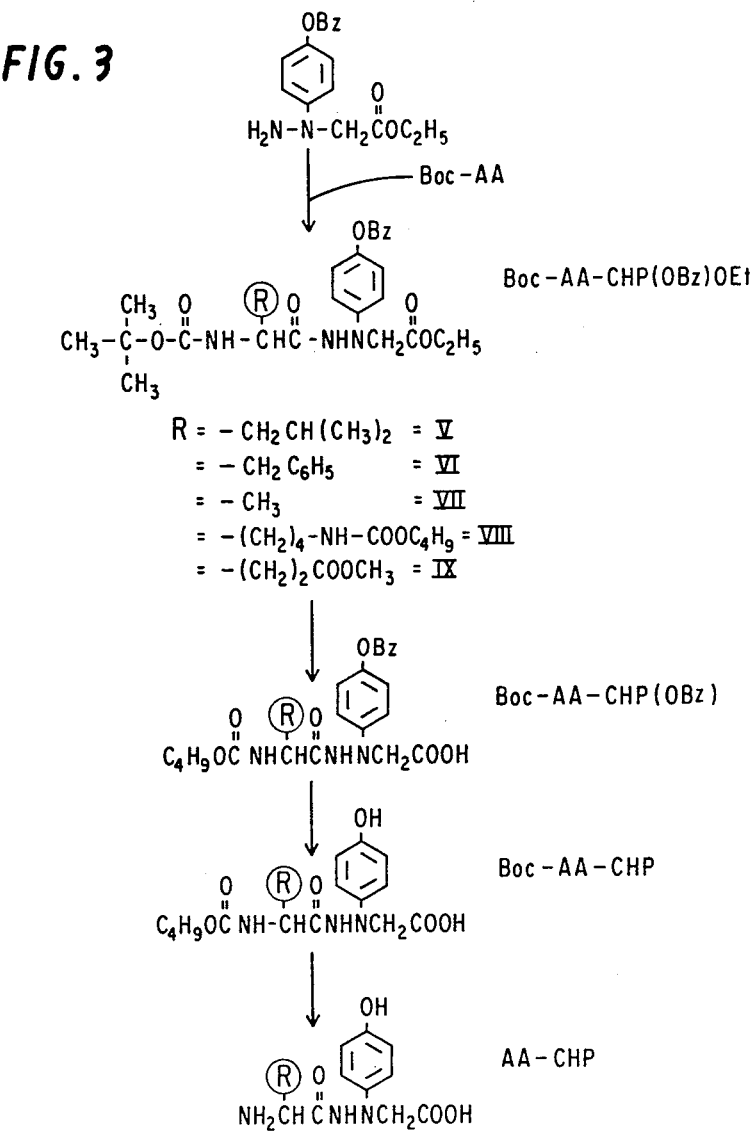

EXAMPLE 3 (See FIG. 3)

Synthesis of β-N-(N-tert-butoxycarbonyl-L-Leucyl)-α-N-(carboxymethyl ethyl ester)-p-benzyloxy phenylhydrazine (Boc-Leu-CHP(OBz)OEt) (V)

To $CH_2Cl_2$ (30 cc) were added IV (9.0 gm, 0.03 mole) and N-tert-butoxycarbonyl-L-leucine (Boc-Leu, 8.4 gm, 0.036 mole) with stirring. After cooling to 4° C. under $N_2$ dicyclohexylcarbodiimide (DCCI, 7.4 gm, 0.036 mole) was added and stirring continued for 18 hours, then EtOAc (300 cc) was added and dicyclohexylurea (DCCU) ws filtered off. The solvent was rotoevaporated leaving a yellow oil. $Et_2O$ was added and the solution was extracted sequentially with 1N HCl, 0.1N NaOH, $H_2O$, then dried over $Na_2SO_4$, filtered and rotoevaporated down to a white solid (V). This was washed with pet ether and filter dried. Yield: 15 gm (97%).

EXAMPLE 4

Synthesis of β-N-(N-tert-butoxycarbonyl-L-phenylalanyl)-α-N-(carboxymethyl ethyl ester)-p-benzyloxyphenylhydrazine(BOC-Phe-CHP(OBz)OEt)(VI)

To dry THF (20 cc) cooled in an ice bath and under $N_2$, N-tert-butoxycarbonyl-L-phenylalanine (Boc-Phe, 3.0 gm, 0.011 mole) and IV (3.0 gm, 0.01 mole) was added and stirred until completely dissolved. DCCI (2.4 gm. 0.012 mole) was added with stirring and reacted overnight. EtOAc (200 ml) was added the DCCU filtered off and solvent removed by rotoevaporation. The resulting oil was dissolved in $Et_2O$ and extracted sequentially with 1NHCl, 0.1N NaOH and $H_2O$. The organic fraction was separated, then dried over $Na_2SO_4$, filtered and rotoevaporated leaving a white solid. This solid was washed with pet ether and filter dried. Yield: 5.0 gm (91.4%).

EXAMPLE 5

Synthesis of β-N-(N-tert-butoxycarbonyl-L-alanyl-α-N-(carboxymethyl ethyl ester)-p-benzyloxy-phenylhydrazine (Boc-Ala-CHP(OBz)OEt)(VII)

N-Tert-butoxycarbonyl-L-alanine (Boc-Ala, 2.4 gm, 0.013 mole) and IV (3.0 mole) were dissolved in THF (15 cc) and cooled in an ice bath under a $N_2$ atmosphere. DCCI (2.4 gm, 0.012 mole) was added with stirring and allowed to react overnight. EtOAc (200 cc) added and the DCCU was filtered off.

The solvent was rotoevaporated and the remaining oil was taken up in $Et_2O$ and extracted successively with 1N HCl, 0.1N NaOH, $H_2O$. The organic layer was separated, dried over $Na_2SO_4$, filtered and rotoevaporated leaving an off-white solid. This was dried with the high vacuum pump overnight. Yield: 4.3 gm (91%). The product (VII) could be recrystallized by dissolving the compound in the minimum quantity of $Et_2O$ and then pouring it into a 30-50 fold volume of pet ether and allowing it to stand at room temperature overnight, yielding white crystals.

EXAMPLE 6

Synthesis of
β-N-(N,N¹-ditert-butoxycarbonyl-L-lysinyl)-α-N-(carboxymethyl ethyl ester)-p-benzyloxyphenylhydrazine
(Boc-Lys-CHP(OBz)OEt)(VIII)

IV (3.0 gm, 0.01 mole) and N,N¹-di-tert-butoxycarbonyl-L-lysine(α-ε-di-Boc-Lys, 4.2 gm, 0.012 mole) were dissolved in THF (20 cc) under $N_2$ and cooled in an ice bath. DCCI (2.4 gm, 0.012 mole) was added and the reaction stirred overnight. EtOAc (200 cc) was added and DCCU was filtered off. The solvent was rotoevaporated and the remaining oil taken up in $Et_2O$, extracted sequentially with 1N HCl, 0.1N NaOH, $H_2O$ and dried over $Na_2SO_4$, filtered and rotoevaporated again to leave a thick yellow oil. This was dried on a high vacuum pump for 24 hours. Yield: 6.2 gm (98.5%). The light beige product could be precipitated from $Et_2O$-Pet ether similar to VII.

EXAMPLE 7

Synthesis of β-N-(N-tert-butoxycarbonyl-L-glutamyl γ-methyl ester)-α-N-(carboxymethyl ethyl ester)-p-benzyloxyphenylhydrazine(BOC-γ-OMe-Glu CHP(OBz)OEt)(IX)

N-tert-butoxycarbonyl-L-glutamyl-γ-methyl ester(-Boc-OMe-Glu, 5.0 gm, 0.02 mole) and IV (5.5 gm, 0.018 mole) were dissolved in THF (25 ml) under $N_2$ and cooled in an ice bath. DCCI (4.4 gm, 0.021 mole) was added and allowed to react overnight. EtOAc (300 ml) was added and DCCU filtered off. The solvent was rotoevaporated off leaving a yellow oil. $Et_2O$ (150 ml) was added and the solution extracted with 1N HCl, 0.1N NaOH, $H_2O$ and dried over $Na_2SO_4$, filtered and rotoevaporated down to an off-white solid. Yield: 9.4 gm (96%).

EXAMPLE 8 (See FIG. 3)

Synthesis of β-L-Amino Acid-(α-N-carboxymethyl)-p-hydroxyphenylhydrazines(AA-CHPs) (X, XI, XII, XIII, XIV)

The respective BOC-AA-CHP(OBz)OEt compound (1 ester equivalent) (i.e., V, VI, VII, VIII, IX) was dissolved in a stirred solution of EtOH and THF (1:1) at room temperature so that the concentration was about 1M. To this was added 1N NaOH (2.1 ester equivalents) and the de-esterification was allowed to proceed overnight. When the reaction was complete, as judged by SG-TLC the reaction solution was extracted with $Et_2O$, the aqueous layer separated, acidified with 1N HCl and extracted into $Et_2O$ followed by EtoAc and then the organic fractions were combined, dried over $Na_2SO_4$, filtered and the solvents rotoevaporated off. The products were sufficiently pure to use in the next reaction. Yields: 71–93%

$R_f$(SG-TLC, EtOAc/EtOH(3:1));
BOC-Leu-CHP(OBz)=0.42   Boc-Glu-CHP(OBz)-0.34
BOC-Phe-CHP(OBz)=0.38   di-Boc-Lys-CHP(OBz)=0.40
Boc-Ala-CHP(OBz)=0.27.

Removal of protective benzyl group by hydrogenation

The respective Boc-AA-CHP(OBz) compounds (2–6 gm) were dissolved in dioxane (20–50 ml) and glacial acetic acid (HAc)(10–15 ml) and the solution was partially deoxygenated by bubbling $N_2$ gas through it for several minutes before the palladium on carbon catalyst (Pd/C)(200–300 mgm) was added and the compound was then hydrogenated for 24–48 hours (40–50 psi $H_2$). After hydrogenation was complete, as judged by SG-TLC, the catalyst was filtered off and the filtrate was rotoevaporated down to clear to light brown oils. These were dried overnight using a high vacuum pump and the resulting solid or oil was washed with $Et_2O$. In the case of the Leu, Phe and Ala derivatives, the solid was then filter dried and weighed. For the lysyl and glutamyl derivatives, the resulting oils were dissolved in $Et_2O$ and, upon standing, a light beige solid precipitated out. This was filtered off, washed with $Et_2O$ again and filter dried. Yields: 84–98%.

$R_f$(SG-TLC, EtoAc/EtOH(3:1));
BOC-Leu-CHP 0.27   di-Boc-Lys-CHP=0.04
BOC-Phe-CHP 0.27   Boc-Glu-CHP=0.28
BOC-Ala-CHP 0.11.

Removal of the Boc Protecting Group

The respective Boc-AA-CHP was then deblocked by adding it to distilled trifluoroacetic acid (TFA, 15 ml/gm Boc-AA-CHP) under $N_2$ and cooled in an ice bath. The reaction was stirred for ½ hour and then poured directly into anhydrous $Et_2O$ (100 cc $Et_2O$/10 cc TFA). The desired product precipitated out immediately as a white solid (TFA salt). After continued stirring for ½ hour, the solid was filtered off and, if hygroscopic, redissolved in the minimum quantity of EtOH which was then rotoevaporated off and the remaining solid dried with a high vacuum pump overnight. Once dry, all the compounds (as the TFA salt) are white solids, stable at room temperature.

For analytical purposes, the Leu-CHP (X) and Phe-CHP (XI) derivatives were repurified by dissolving in water (pH 11) and acidifying to neutrality with 1N HCl. The precipitate (off-white) was filter dried and washed with EtOAc. The Ala-CHP (XII) derivative was recrystallized from boiling water. The Lys-CHP (XIII) and Glu-CHP (XIV) derivatives were left in their TFA salt form. Yield: 70–80%.

Figure 4:
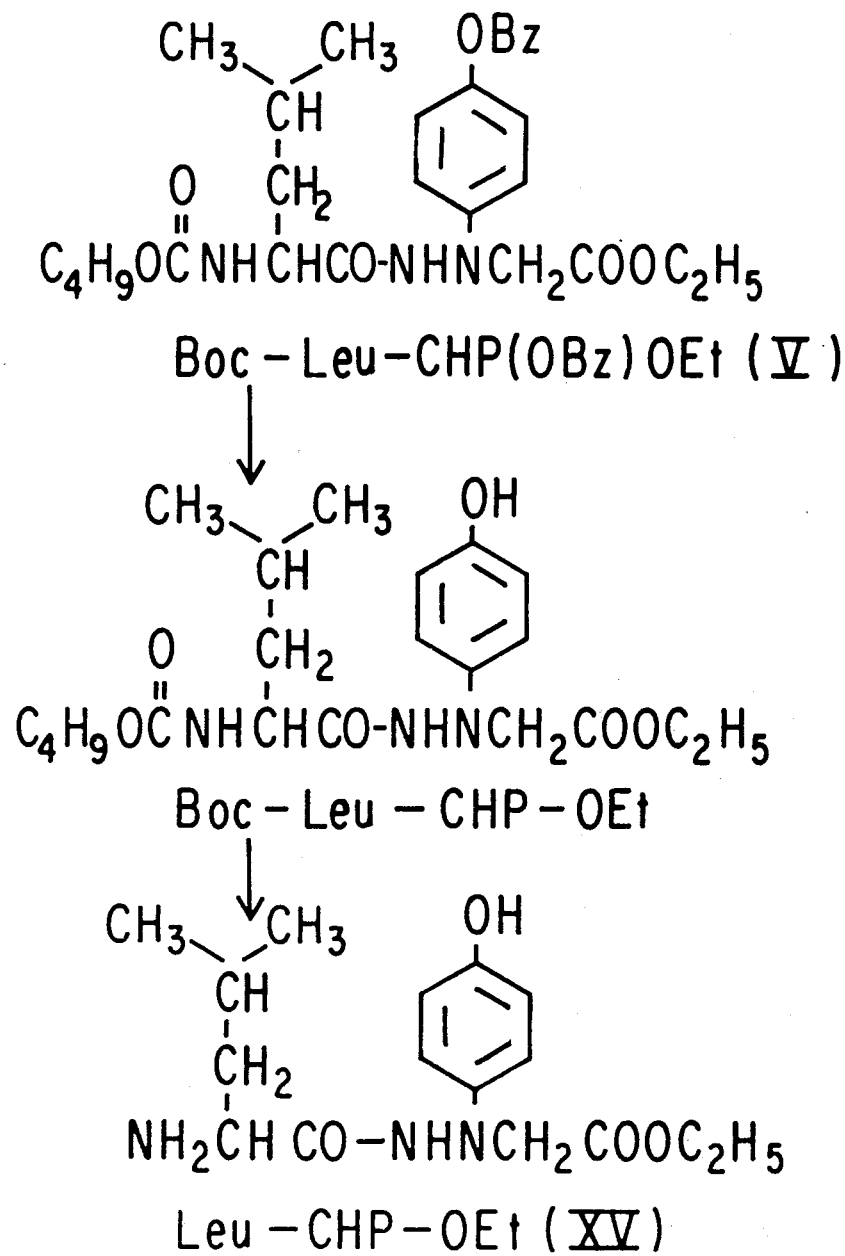

EXAMPLE 9 (See FIG. 4)

Synthesis of β-N-(L-leucyl)-α-N-(carboxymethyl ethyl ester)-p-hydroxyphenylhydrazine (Leu-CHP-OEt) (XV)

Boc-Leu-CHP(OBz)OEt (3.0 gm, 0.0058 mole) was dissolved in dioxane (40 ml) and HAc (10 ml) and catalytically hydrogenated (Pd/C) (45–50 psi $H_2$) for 24 hours. The catalyst was filtered off and the solvent rotoevaporated down to an oil which was further dried with the high vacuum pump overnight. Yield: 2.2 gm (Boc-Leu-CHP-OEt, 89%)

This product (1.0 gm, 0.0024 mole) was then deblocked with distilled TFA (6 cc) at 0° C. under $N_2$ for ½ hour. The reaction solution was poured directly into dry $Et_2O$ (200 ml) and pet ether (50 ml) and the white product precipitated out within one hour. Yield: 0.9 gm (3/2 TFA.Leu-CHP-OEt) Yield=77%.

Figure 5:
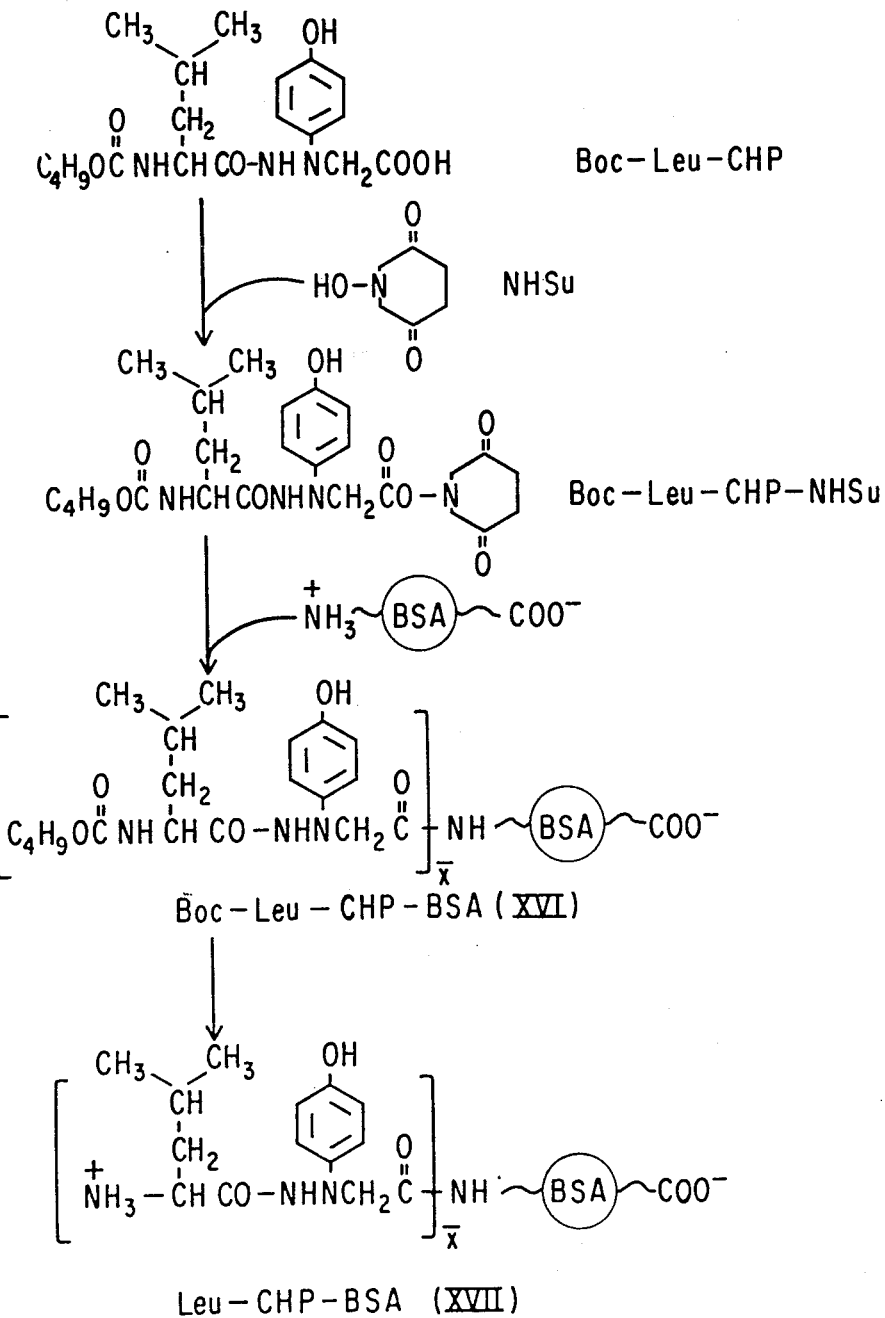
Figure 6:
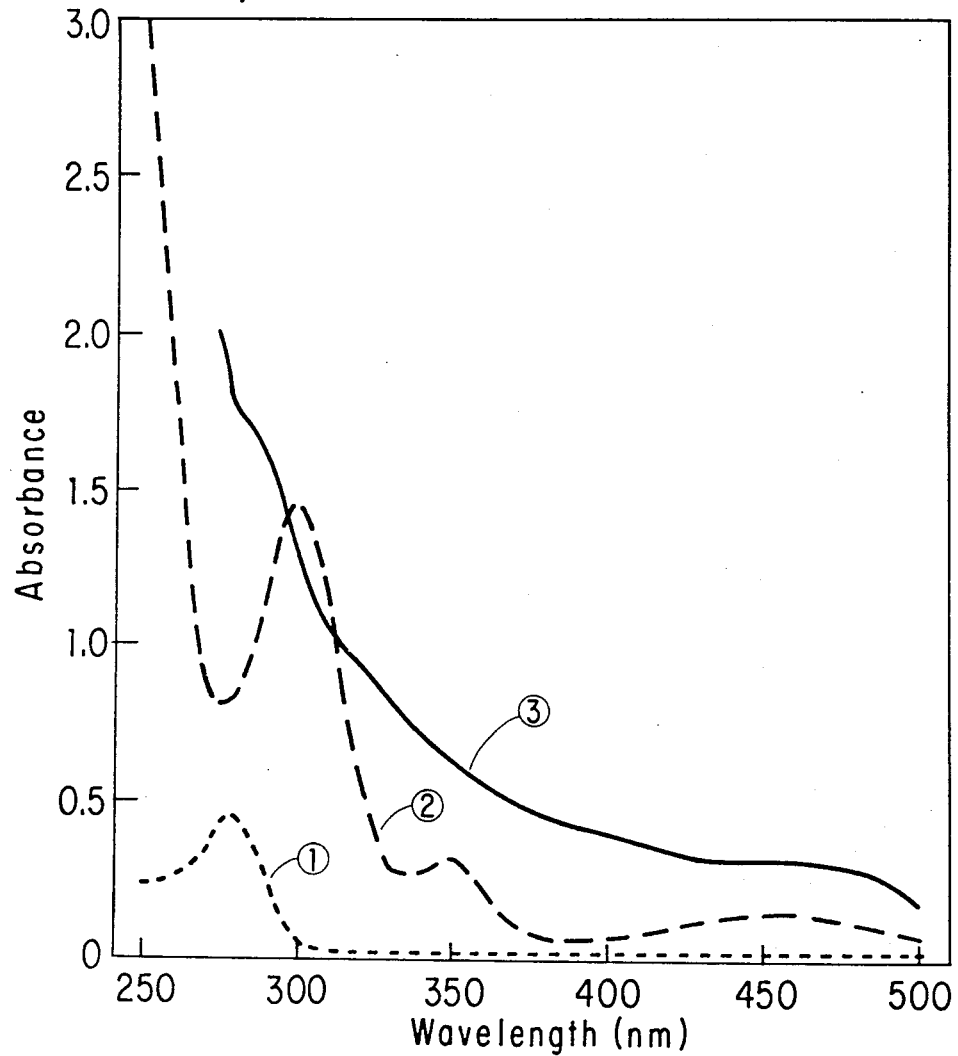

EXAMPLE 10 (See FIG. 5)

Coupling of Leu-CHP to bovine serum albumin

Boc-Leu-CHP (3.5 gm, 0.0089 mole) and N-hydroxysuccinimide (NHSu) (2.0 gm, 0.07 mole) were added to $CH_2Cl_2$ (20–30 ml) with stirring. The reaction solution was cooled in an ice bath and placed under $N_2$. DCCI (3.0 gm, 0.0146 mole) was added and the reaction was allowed to proceed for 18 hours. EtOAc was added and the DCCU was filtered off. After extracting with saturated NaHCO3, the organic fraction was separated, dried over Na2SO4, filtered and rotoevaporated down to a light yellow oil which solidified after drying overnight with the high vacuum pump. This product was used directly in the coupling reaction. Yield: 3.6 gm (83%).

In a 200 ml 3N-RBF fitted with an overhead mechanical stirrer bovine serum albumin (BSA, 2.76 gm) was dissolved with stirring into saturated NaHCO3 (10 ml). To this was added in 2 ml increments a solution of Boc-Leu-CHP-NHSμ.(3.2 gm, 0.0065 mole) in EtOH (10 ml). Enough 1N NaOH was added to raise the pH to 8.0 and the reaction was stirred. After 1 hour the reaction solution became viscous and more saturated NaHCO3 (20 ml) and EtOH (5 ml) were added. This was stirred at room temperature overnight. The protein forms a viscous orange gel overnight and more H2O (20 ml) was added. After 48 hours of coupling time, the reaction solution had changed from orange to brown. The reaction mix was poured into dialysis tubing (30×3 cm) and dialyzed against 20 volumes of demineralized H2O which was changed every day for 6 days. The modified protein product within the dialysis tubing was dark brown. After 6 days, the dialysis tubing was opened and filtered twice: first through #41 Whatman filter paper (coarse), then #42 Whatman filter paper (ultrafine). The clear brown filtrate was then gradually acidified with 1N HCl to pH 4.0. The modified protein product precipitated out immediately as a beige solid. This was allowed to stand overnight at 4° C. and then centrifuged at 10000 rpm×20 min. The clear supernatant was discarded and the protein precipitate was shell-frozen in a dry ice-acetone bath and vacuum dried with a high vacuum pump. The product was a brown solid. Yield: 3.0 gm (80.6%) (based on 100% coupling to 61 Lysyl residues per alubmin molecule)

Boc-Leu-CHP-BSA (XVI) (1.0 gm) was added to distilled TFA (50 ml) under N2 at 4° C. for ½ hour with stirring. The reaction suspension was then added to dry Et2O (200 ml) and the product filter dried and pulverized with a mortar and pestle. The product XVI is brown in color. Yield: 1 gm (99%).

Figure 7:
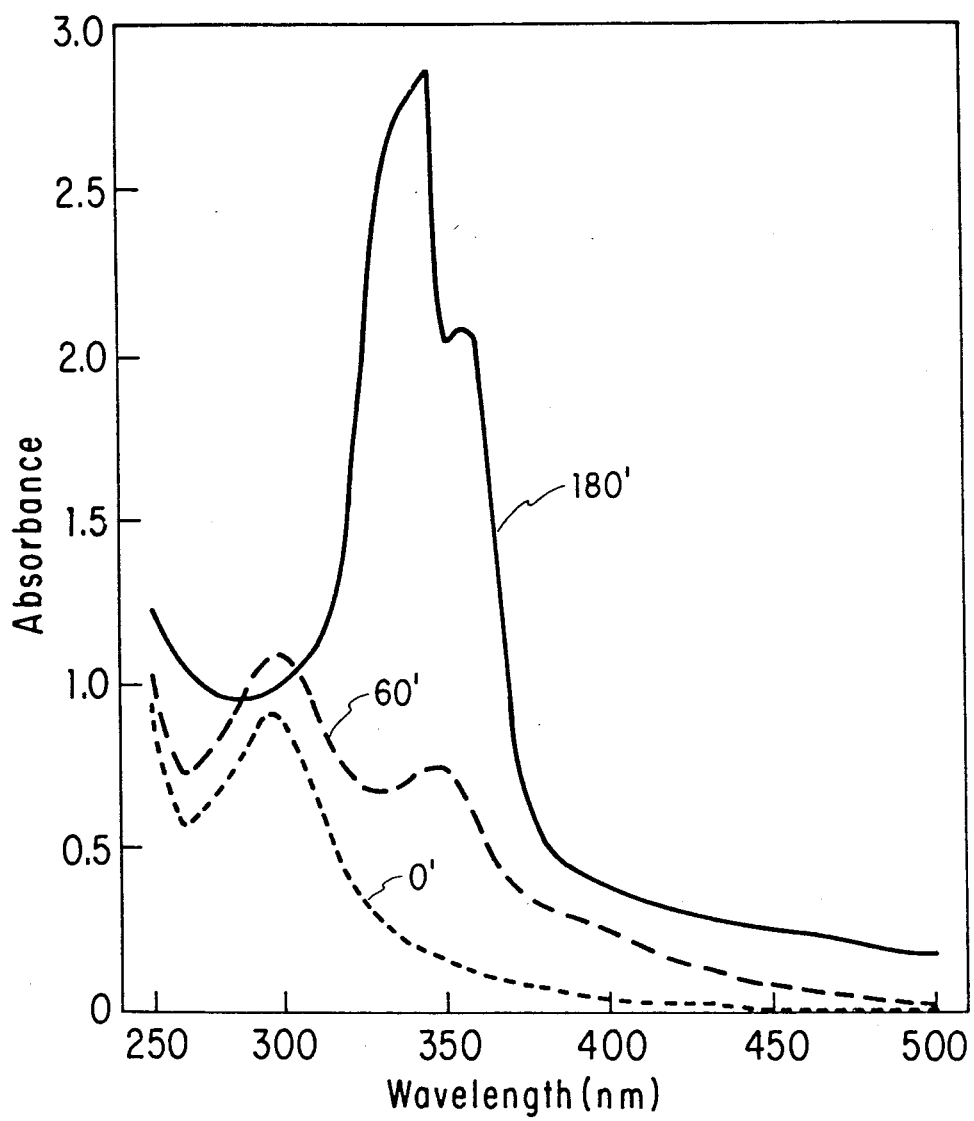

EXAMPLE 11 (See FIG. 7)

Leucine Aminopeptidase In Vitro Hydrolysis

Leucine Aminopeptidase (LAP), type III-CP (Sigma) was stored at 0°–4° C. in 0.75M saturated ammonium persulfate, 0.1M Tris and 0.005M MgCl2 (pH 8) and contained 210 U/ml. Prior to the hydrolysis experiment, LAP (50λ) was activated by incubating it in 0.025M MnCl2 (0.2 ml), 0.5M Tris.HCl buffer (pH 9.0, 0.2 ml) and demineralized and ultra-filtered H2O (0.6 ml) for at least 2 hours at 37° C. To each sample test tube was added AA-CHP (1.5 mg) in 0.02M Tris HCl buffer (pH 9.0, 0.5 ml) so that the final concentration was 1 mg/ml AA-CHP. The hydrolysis reaction was allowed to proceed for up to 12 hours and then TLC's were performed by spotting the reaction solution (2–3 μl) on cellulose plates and developing them in Butanol (20 ml)/HAc(4ml)/Pyridine(13.3 ml)/H2O (16 ml) solvent system. They were dried and sprayed with 0.2% Ninhydrin in EtOH and the color was developed at 85° C. for 5 minutes. The in vitro hydrolysis of Leu-CHP by LAP was also concomitantly studied by scanning spectrophotometry at different times after the start of incubation with the enzyme. A blank reference cell containing only enzyme and buffer was used.

The enzyme was able to cleave Leu-CHP, Phe-CHP, Ala-CHP, Leu-CHP-OEt and Leu-CHP-BSA but not Lys-CHP, Glu-CHP, or Boc-Leu-CHP.

Figure 8:
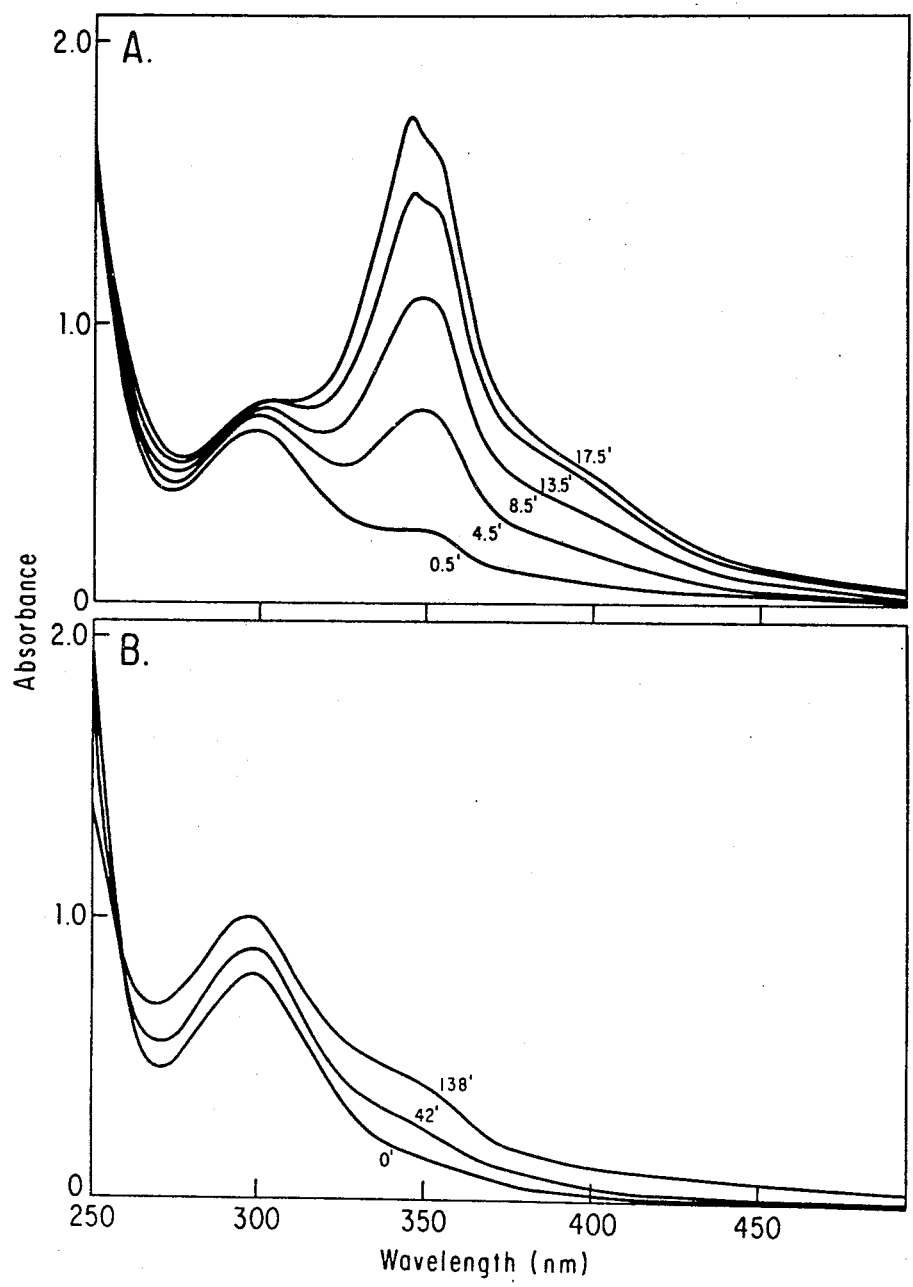

In order to characterize the products of hydrolysis of AA-CHP's, the hydrolysis of Leu-CHP by LAP was studied by absorption spectrophotometry. As shown in FIG. 7, during the hydrolysis of Leu-CHP by LAP at pH 8.5 the original maximum at 300 nm disappeared and another more intense maximum at 350 nm appeared. This spectral change was mimicked by free CHP-OEt alone at pH 9.0 as shown in FIG. 8A. FIG. 8A shows that the absorption maximum of CHP-OEt was at 300 nm and that up to 17.5 minutes after addition of CHP-OEt (0.2 mg) in DMSO (0.02 ml) to 0.01M Tris buffer at pH9.0 (3.0 ml) the absorbance at 300 nm continued to increase. This was also true for the new maximum at 350 nm and for a second new "maximum" which appeared as a low, broad "peak" merging with 350 peak and centered at about 400 nm. However, by 22 minutes (not shown) the absorbance at 300 and 400 nm had diminished in intensity while the 350 maximum continued to increase, albeit at a slower rate. At pH 7.0 (FIG. 8B),

TABLE 1

| Compound | Mol. Wt. | % Yield | Mp(°C.) | Analytical Data Calc. C | H | N | Obs. C | H | N | $R_f$ | $[\alpha]_D^{20}$ |
|---|---|---|---|---|---|---|---|---|---|---|---|
| II | 285.3 | 80 | 64–65 | 71.56 | 6.71 | 4.91 | 71.88 | 6.66 | 4.65 | .59[a],.27[b] | |
| III | 314.3 | 68.5 | 67.5–69 | 64.96 | 5.77 | 8.91 | 64.84 | 5.73 | 8.95 | .57[a],.41[b] | |
| IV | 300.36 | 71 | 95–96 | 67.96 | 6.72 | 9.33 | 67.86 | 6.76 | 9.12 | .44[a],.065[b] | |
| V | 513.64 | 97 | 114–115.5 | 65.48 | 7.65 | 8.18 | 65.48 | 7.65 | 8.37 | .83[a] | |
| VI | 547.65 | 91.4 | 133–135 | 67.99 | 6.81 | 7.67 | 67.99 | 7.02 | 7.59 | .81[a] | |
| VII | 471.55 | 91 | 88–90 | 63.68 | 7.05 | 8.91 | 63.69 | 7.13 | 8.95 | .76[a] | |
| VIII | 628.77 | 98.5 | 59–61 | 63.04 | 7.70 | 8.91 | 62.80 | 7.89 | 8.95 | .59[a] | |
| IX | 543.62 | 96 | 92–94 | 61.86 | 6.86 | 7.73 | 61.64 | 6.77 | 7.74 | .65[a] | |
| X | 295.34 | 75 | 222–224 | 56.92 | 7.17 | 14.23 | 56.76 | 7.24 | 14.15 | .82[c] | +23.1[k] |
| XI | 338.36[d] | 70 | 215–216 | 60.35 | 5.96 | 12.42 | 60.41 | 5.94 | 12.20 | .79[c] | +27.9[g] |
| XII | 266.77[l] | 80 | 227–229 | 49.53 | 6.23 | 15.75 | 49.46 | 6.30 | 15.67 | .44[c] | +24.1[m] |
| XIII | 556.41[e] | 80 | 198–199 | 38.86 | 4.71 | 10.07 | 38.58 | 4.85 | 10.31 | .16[c] | +20.5[h] |
| XIV | 377.3[f] | 80 | 200–201 | 44.57 | 4.94 | 11.13 | 44.17 | 5.00 | 11.14 | .29[c] | +17.2[i] |
| XV | 494.4[j] | 77 | 190–191 | 48.92 | 5.72 | 9.01 | 48.70 | 5.66 | 9.32 | .98[c] | |

[a]= Et2O/Pet Ether (1:1), [b]= CCl4/CH2Cl2 (2:1) Both on SG—TLC. [c]= Cellulose TLC; Butanol (20): Pyridine (13.3): H2O (16): Acetic Acid (4) [d]= ½ mole H2O present; [e]= 2Tfa.1H2O salt; [f]= ½ Tfa.½ H2O salt; [g,c]= 1.5 of Phe—CHP.½ H2O; [h,c]= 1.5 of Lysyl—Tfa.1H2O; [i,c]= 1.5 of Glu—CHP.½ Tfa.½ H2O; [k,c]= 1.5; [j]= 3/2 Tfa salt; [l]= ½ H2O present; [m,c]= 1.5 of Ala—CHP.½ H2O.

the absorbance at 300 nm continued to slowly increase in intensity even up to 90 minutes after dissolving CHP-OEt (0.2 mg) in DMSO (0.02 ml) into 0.05M Phosphate buffer (3 ml). Furthermore, a second maximum at 350 nm developed but it remaind smaller in intensity than the 300 nm peak.

Because of the obvious instability of CHP-OEt in aqueous solution and because of the apparent multiplicity of absorbing species appearing during its rearrangement and elimination reactions to form quinones and iminoguinones, this process was further characterized by including in the reaction mixture a reducing agent (NaBH$_4$) a nucleophile which was not also a reducing agent (Lysine) or 3 mercaptoproprionic acid (3-MPA) which could function both as a nucleophile and as a reducing agent.

Figure 9:
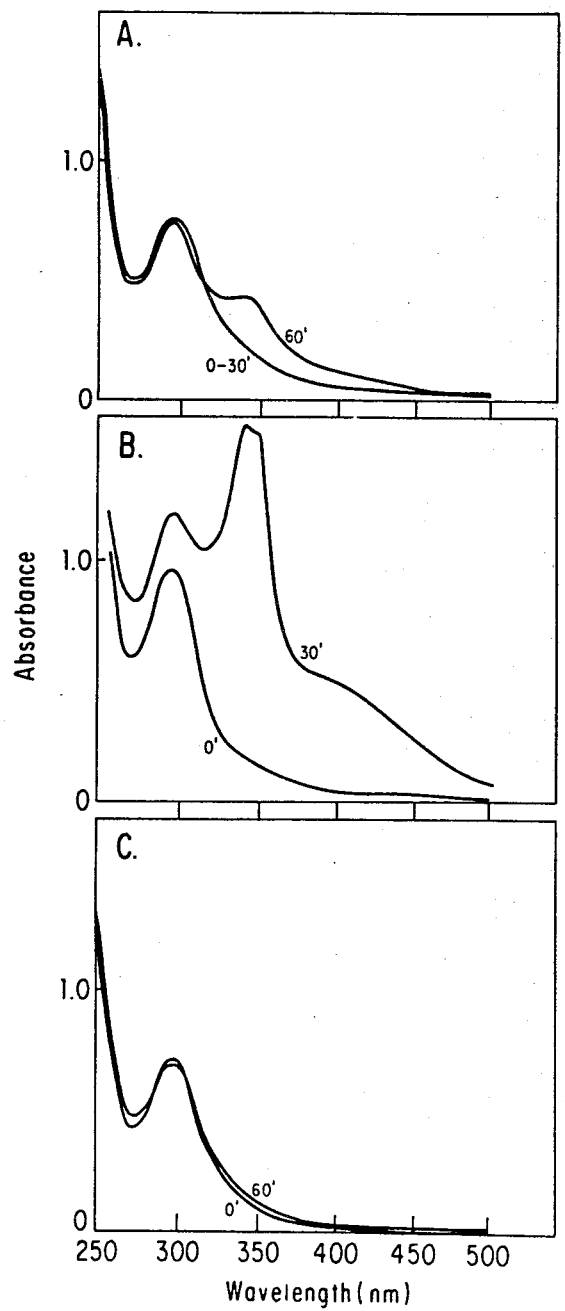

As shown in FIG. 9A, a ten-fold excess of NaBH$_4$, a reducing agent, completely abolished formation of the 350 nm peak at pH 9.0. Once all the NaBH$_4$ had decomposed (after 50 minutes), the peak at 350 nm could be seen. In FIG. 9B, a ten-fold excess of Lysine, a nucleophile but not a reducing agent, had little if any effect on the development of the 350 nm peak. On the other hand, a ten-fold excess of 3-MPA, both a nucleophile and a reducing agent, completely abolished any spectral change over the time span of several hours. (FIG. 9C).

Table 2 summarizes the results of several separate experiments involving the reactions of CHP-OEt, CHA-OEt, pIQ-OEt and pBQ (0.5–1.0 mM) with various nucleophiles (lysine, 3-MPA) reducing agents (NaBH$_4$, 3-MPA) and oxidizing agents (NaIO$_4$, O$_2$) in ten-fold molar excess in Tris-HCl buffer (0.05M, pH 9.0).

In these studies, CHP-OEt, CHA-OEt and pBQ* were all pure compounds, thus, their absorption could be unequivocably assigned, pIQ-OEt was generated by the autoxidation of CHA-OEt in solution and its presence was noted by the appearance of one absorbance maximum at 400 nm and the development of a distinct yellow color to a previously clear solution of CHA-OEt. As shown in Table 2, there was a striking similarity in the absorption maxima that resulted when CHP-OEt was reacted with Lysine (350 nm) and 3-MPA (300 nm) with those that occur when pBQ was reacted with these same compounds. On the other hand, there was a dissimilarity between the spectra of CHP-OEt and CHA-OEt. CHA-OEt was oxidized by O$_2$ or NaIO$_4$ to the pIQ-OEt with a $\lambda_{max}$=400 nm whereas NaIO$_4$ had no effect on the rate or nature of spectral change that occurred when . . .

TABLE 2

Summary of Spectral Study Experiments With CHP—OEt, (IVa) CHA—OEt, (IIa), and p-Benzoquinone (pBQ) at pH 8–9

| Compound | Initial Maximum (nm) | Compound Added | Final Maximum (nm) |
|---|---|---|---|
| CHP—OEt | 300 | none | 350 |
| CHP—OEt | 300 | Lysine | 350 |
| CHP—OEt | 300 | 3-MPA | 300 |
| CHP—OEt | 300 | NaBH$_4$ | 300 (350$^a$) |
| CHP—OEt | 300 | NaIO$_4$ | 350$^b$ |
| CHA—OEt | 300 | none | 300, 400$^c$ |
| CHA—OEt | | NaIO$_4$ | 300, 400$^d$ |
| pIQ—OEt + CHA—OEt | 300, 400 | Lysine | 300 |
| pIO—OEt + CHA—OEt | 300, 400 | 3-MPA | 300 |
| pBQ | 240 | Lysine | 350 |
| pBQ | 240 | 3-MPA | 300 |

$^a$Appears after NaBH$_4$ has decomposed.
$^c$Formation of p-iminoquinone (pIQ—OEt) via autoxidation.
$^b$No change in rate of rearrangement.
$^d$Formation of pIQ—OEt accelerated when CHP—OEt was dissolved in alkaline H$_2$O.

When CHA-OEt was allowed to autoxidize to pIQ-OEt and then reacted with Lysine, the 400 nm peak disappeared and only the 300 nm peak remained, whereas lysine had no effect on the spectral changes that occurred when CHP-OEt was dissolved in alkaline H$_2$O. Both CHP-OEt and CHA-OEt, when reacted with 3-MPA, showed stable maxima at 300 nm for several hours.

Figure 2:
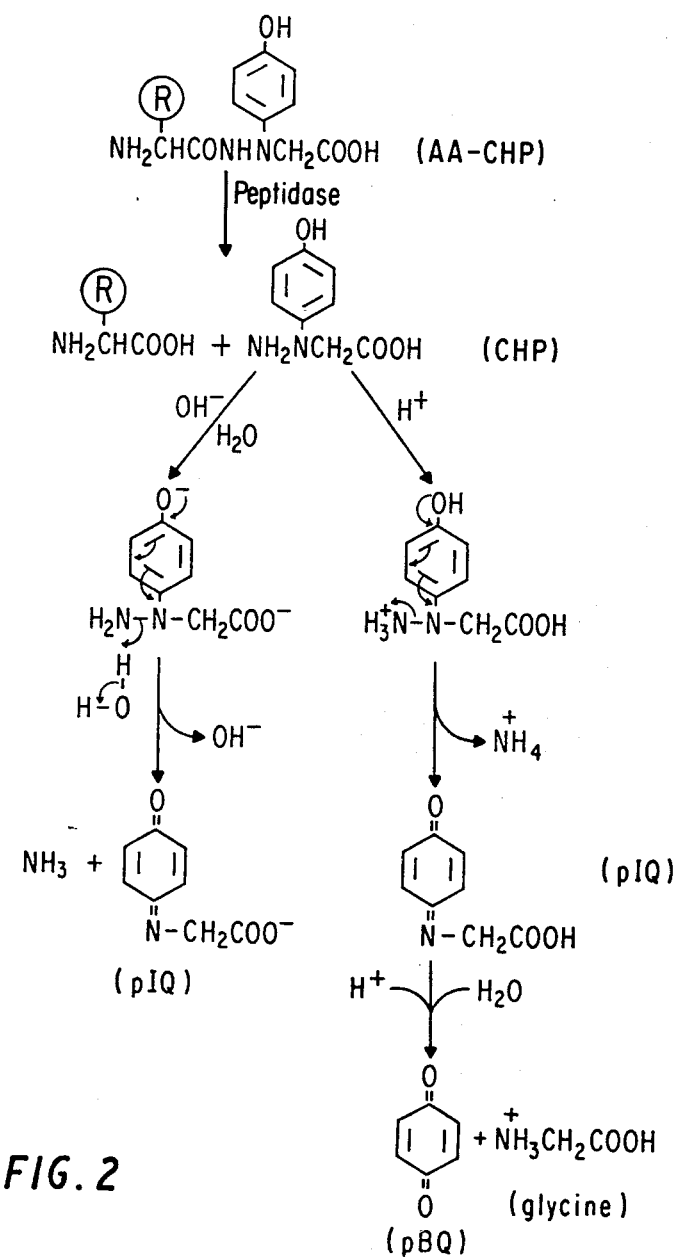

The proposed explanation for these data is given in FIG. 10. This scheme postulates a central role for the p-iminoquinone (pIQ-OEt) the product of reaction A or H. In the case of reaction A, pIQ-OEt is generated by the spontaneous rearrangement of CHP-OEt to give the iminoquinione by losing ammonia. This rearrangement can be acid or base catalyzed (see FIG. 2). The present data does not allow differentiation between these mechanisms. It is important to note that from FIG. 10, the maxima at 350 nm are assigned to disubstituted aminophenols, the products of the reaction sequence ABCD. Thus, even though the development of the peak at 350 nm was severaly retarded when CHP-OEt was dissolved in water (pH 7.0) (FIG. 8B). This is only a reflection of the decreased rate of formation of these final products (BCD) at this more acidic pH and not a measure of the generation of pIQ-OEt. The fact that at pH 7.0 a peak at 400 nm did not develop when CHP-OEt was incubated in aqueous solution may be explained by the very low $\epsilon_{400}$ for pBQ. Thus, when pIQ-OEt underwent disassociation at this pH giving pBQ and glycine ethyl ester (E), pBQ would have made an insignificant contribution to the absorbance at 400 nm. At alkaline pH, CHP-OEt itself can attack pIQ-OEt as a nucleophile (B) as can lysine. The oxidation of that product ($\lambda_{max}$=300 nm) by either O$_2$ or pIQ-OEt (C) gives a second quinone which can undergo a second nucleophilic attack at one of two sites (D). Thus lysine would not be expected to have an effect on the development of the peak at 350 nm. That this is the case was borne out in the experiment reported in FIG. 9B. In the presence of NaBH$_4$, any pIQ-OEt that was formed was immediately reduced to CHA-OEt (G). Once the NaBH$_4$ had decomposed, any pIQ-OEt generated was able to follow pathway BCD (FIG. 9A). On the other hand, 3-MPA could react with pIQ-OEt (F) or reduce it (N) and reduce any dissolved oxygen by forming a disulfide (I,O). This would effectively quench any reoxidation of the pIQ-OEt-3-MPA adduct or CHA-OEt, thereby inhibiting the formation of a disubstituted aminophenol and the development of the 350 nm peak. In reaction H, the generation of pIQ-OEt from CHA-OEt depends on an alkaline pH and the presence of a suitable oxidizing agent (e.g., O$_2$, NaIO$_4$) and in turn, reduces that agent (H). Once oxidized to pIQ-OEt, the quinone was fairly stable because CHA-OEt is a poor nucleophile (unlike CHP-OEt). If lysine was added, however, to a solution of pIQ-OEt, only the mono-adduct was formed because the supply of an oxidizing agent (e.g., $O_2$, had been depleted in the formation of pIQ-OEt. This contrasted strongly with CHP-OEt, which can spontaneously rearrange to pIQ-OEt and hence did not require oxygen for reaction A or an external oxidizing agent for reaction C, since the continued production of pIQ-OEt (A) ensured the re-oxidation of the mono-adduct (C) and formation of the disubstituted products (D). When pBQ was reacted with 3-MPA and Lysine, the spectral results obtained were very similar to those achieved when these two compounds were reacted with CHP-OEt. When a ten-fold excess 3-MPA was added to pBQ at pH 9.0 a peak at 300 nm developed rapidly, but the peak at 350 nm appeared only after several hours. (J). On the other hand, when a ten-fold excess of lysine was reacted with pBQ at pH 9.0, an initial peak at 300 nm (K) was observed which rapidly diminished while a strong peak at 350 nm appeared (M). This 350 nm peak appeared at a faster rate than the 350 nm peak observed when CHP-OEt was dissolved in alkaline water.

From these data. one must infer that CHP-OEt acts both as a quinone and nucleophile, leading to the conclusion that CHP-OEt (in a protic solvent, such as $H_2O$) undergoes a rearrangement resulting in the formation of pIQ-OEt which can then undergo subsequent nucleophilic attack, reoxidation, and nucleophilic attack again depending on the pH and the presence or absence of appropriate nucleophiles and reducing and oxidizing agents. Furthermore, this spontaneous rearrangement of CHP-OEt to pIQ-OEt would not be dependant on the presence or absence of an oxidizing agent (e.g., oxygen) and therefore should be as likely to occur in an hypoxic environment. Since it is well known that quinones are cytotoxic and having established that various AA-CHP's were capable of being enzymatically cleaved by LAP in vitro, and that upon enzymatic cleavage, CHP is released and can undergo a rearrangement to give an iminoquinone, these compounds were next tested for toxicity to leukemia cells.

EXAMPLE 12

In vitro Inhibition of $^3$H-Thymidine Incorporation into DNA of L1210 Murine Leukemia Cells An L1210 murine leukemia cell line was maintained in mice (female DBA/2J strain from the Jackson Laboratory, Bar Harbor, Maine) by transferring every seven days via intraperitoneal (i.p.) injection of $10^5$ cells. L1210 cells were also stored at liquid nitrogen temperature in 2 ml aliquots containing $10^6$ cells/ml in a storage medium consisting of 72% (v/v) RPMI Medium 1640 (Grand Island Biochemicals), 18% (v/v) fetal calf serum, 10% (v/v) dimethylsulfoxide ($Me_2SO$) and 1% Glutamine. The frozen cells maintained their viability for over two years. For all in vitro and in vivo experiments only freshly harvested intraperitoneally grown L1210 cells were used.

Figure 11:
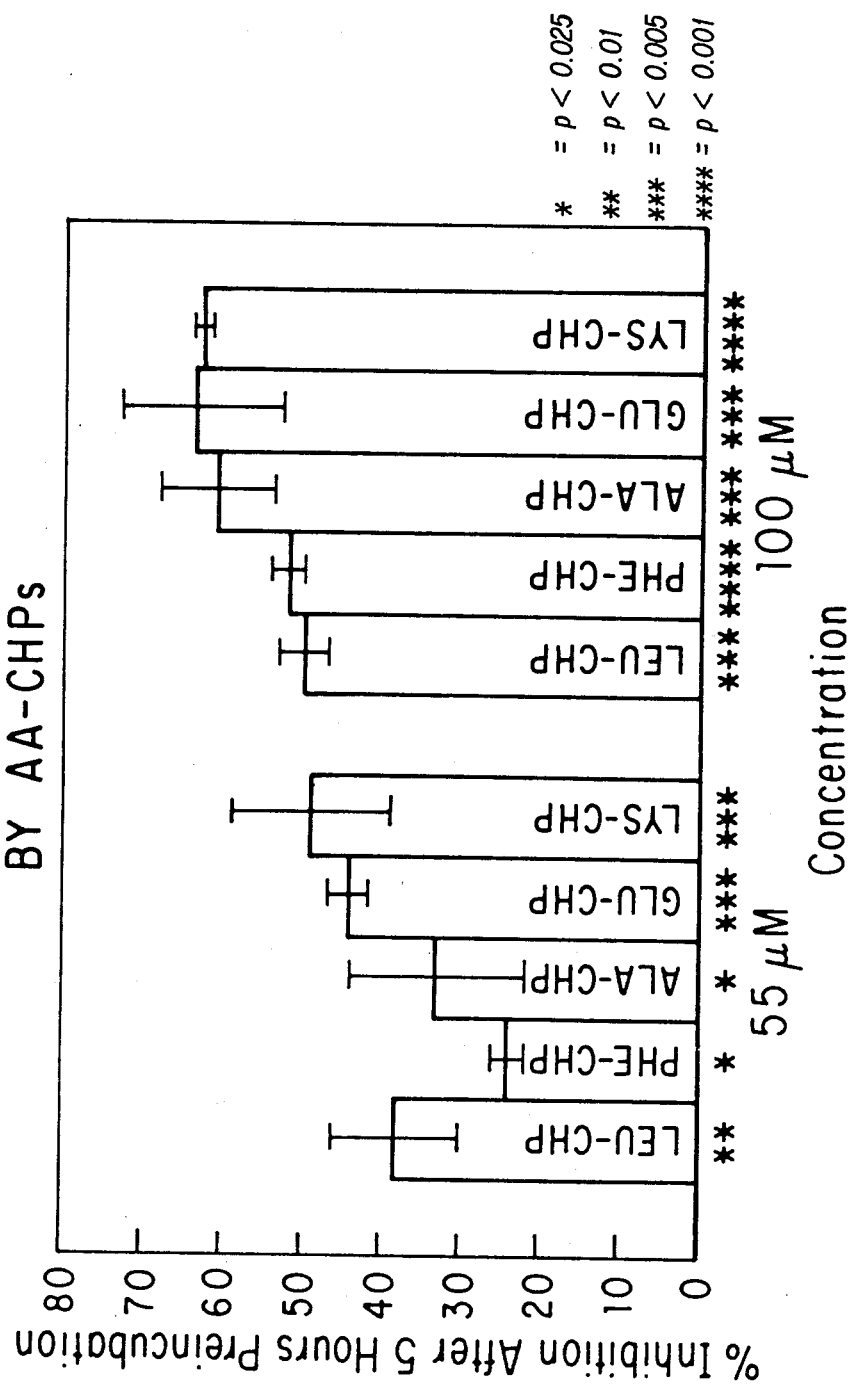
Figure 12:
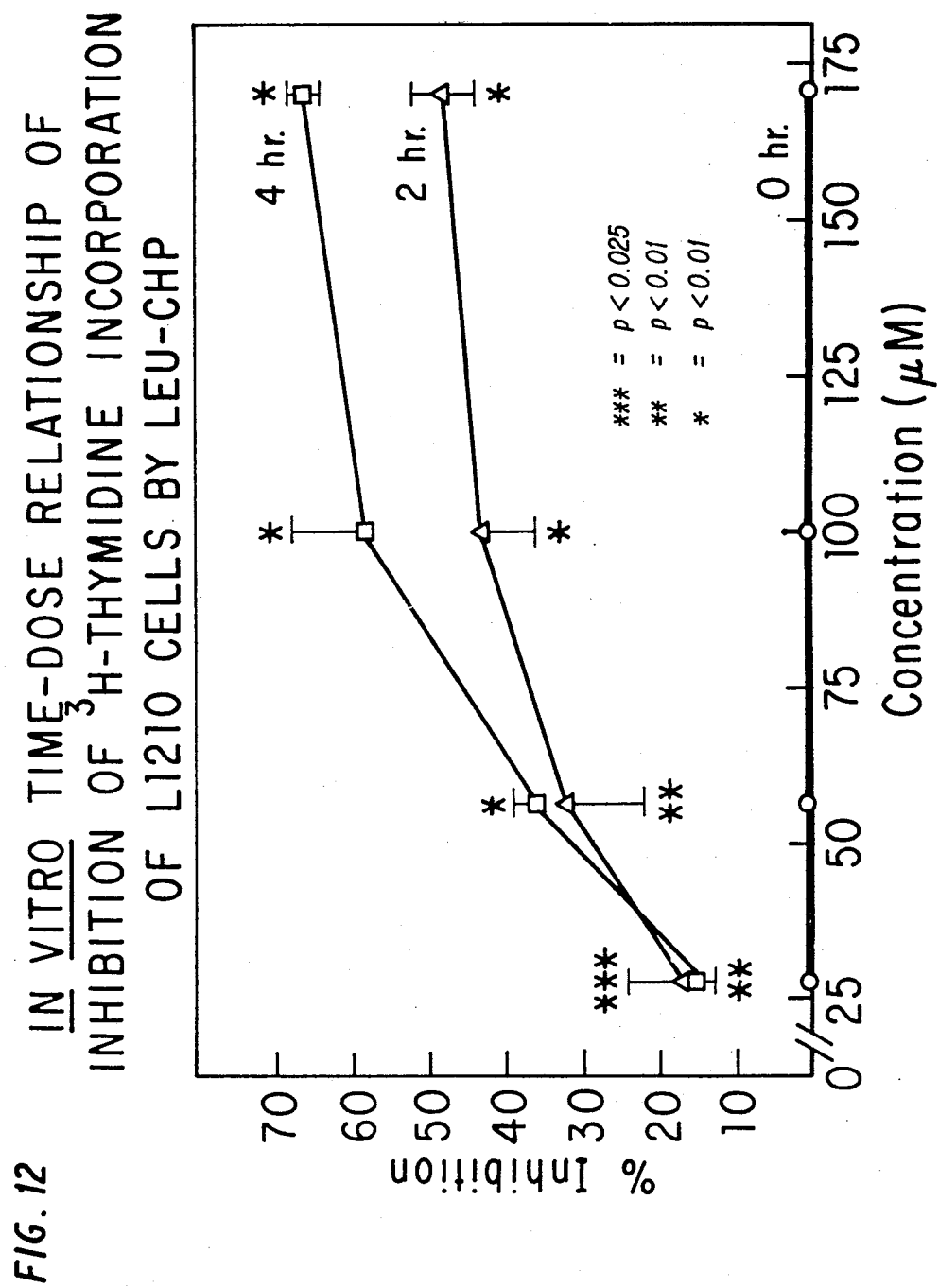

A DBA/2J mouse bearing L1210 cells for 6 days after i.p. inoculation of $1 \times 10^5$ cells was sacrificed by cervical dislocation and, using sterile technique, the abdominal skin was incised and pinned back. Using two 10 ml syringes with 21 gauge needles, one being filled with cold phosphate buffer saline (PBS) (9 ml, pH 7.4) and in 3 ml increments, the solution was injected into the peritoneal cavity through one side and withdrawn with the other syringe through the other side. The light pink cell suspension was then centrifuged at 2000 rpm for 5 minutes and the supernatant was decanted. The cells were resuspended in cold 80% RPMI Medium 1640/20% heat inactivated fetal calf serum (10 ml). After having counted the cells with a hemocytometer and stained them for viability with Trypan blue (usually 99% viable), they were diluted to a final concentration of $1 \times 10^6$ viable cells/ml (unless otherwise noted.) Each test tube then received 100 $\mu$l of the cell suspension and 25 $\mu$l of the test compound or control solution (PBS) and was then incubated at 37° C. under a 95% $O_2$/5% $CO_2$ atmosphere. After 0, 2, 4, 5 or 6 hours preincubation, 3H-Thymidine (1 $\mu$l; 1 $\mu$C) was added and then the incubation was continued for another ½ hour. The cells were then killed and their proteins precipitated with 5% TCA. This was then filtered through Whatman GF/C filter discs, washed three times with 1% TCA, then 95% EtOH and then oven dried for 5 minutes (100° C.). The filter discs were then digested with NCS tissue solubilizer (0.5 ml) and PPO/POPOP in toluene scintillation cocktail (2.0 ml) for ½ hour. To each vial was then added more PPO/POPOP/Toluene cocktail (1.5 ml) and the samples were counted. All determinations were made in triplicate. The results of these experiments are shown in FIGS. 11, 12 and 13. These experiments compared the various compounds at given concentrations (FIG. 11 and FIG. 13) and describe the dependance of the degree of inhibition on both the incubation time and the concentration of a representative AA-CHP (FIG. 12). All of the AA-CHP were roughly equivalent with respect to their ability to inhibit 3H-Thymidine incorporation, and this inhibition increased for each compound as the concentration was increased (FIG. 11).

As shown in FIG. 12, no inhibition of $^3$H-thymidine into DNA was achieved by Leu-CHP if the L1210 cells were exposed to $^3$H-thymidine and Leu-CHP at the same time. As the time of pre-incubation with Leu-CHP or its dose was increased, the degree of inhibition of $^3$H-thymidine incorporation also increased suggesting that either uptake or hydrolysis of Leu-CHP was rate limiting.

Whereas the AA-CHP's required pre-incubation with L1210 cells in order to achieve inhibition of DNA synthesis, the MPD's achieved inhibition of $^3$H-thymidine incorporation in the absence of pre-incubation (i.e., during the half-hour the L1210 cells were exposed to both MPD's and 3H-Thymidine (FIG. 13). While Leu-CHP-BSA was more effective during the first 4 hours of incubation, after 6 hours, there were no differences in inhibition (83%) between Boc-Leu-CHP-BSA (XVI) and Leu-CHP-BSA (XVII) at the concentrations shown.

The observation that these seven structurally different compounds (5 AA-CHP's, 2 MPD's) all inhibited 3H-Thymidine incorporation into DNA combined with the fact that all of these compounds are dipeptide or protein derivatives and not structural analogs of DNA constituents or DNA polymerase substrates indicated that they shared a common mechanism of inhibition which was quite different from such analogs. The common mechanism proposed here is that, upon enzymatic cleavage of the common hydrazide bond, toxic quinones are generated which react with protein (e.g., DNA polymerase-$\alpha$) and non-protein bound (e.g., glutathione) sulfhydryl groups resulting in inhibition of sulfhydryl dependant enzymes and depletion of the intracellular sulfhydryl concentration.

EXAMPLE 13

In Vivo Toxicity and Cysteine "Rescue" Experiments

Experiments were performed which were designed to establish the $LD_{50}$ of the compounds tested and to see whether the toxicity of these compounds could be reduced by exogenously administered cysteine which would increase the intracellular concentrations of reduced sulfhydryl groups to react with quinones that might be generated and hence protect the animal from the toxicity of the AA-CHP's.

Female DBA/2J mice, 8 weeks old, were injected intraperitoneally with test compound solutions (X, XI, XII, XIII, XIV) made up by dissolving the compound in 1N NaOH (1 ml), adding 1N HCl (approximately 1 ml) to pH 7–8 and diluting with PBS (pH 7.4) to give a final concentration of 30 mg/ml. In the case of compounds XVI and XVII, they were first dissolved in 1N NaOH and acidified gradually with 1N HCl to pH 7–8 so that the final maximum concentration was 30 mg/ml. Compound IVa, just prior to injection, was dissolved in DMSO and then added to PBS so that the final concentration was 20 mg/ml in 7% DMSO. The yellow solution was injected immediately because the compound decomposes rapidly in aqueous media.

Cysteine hydrochloride was neutralized with 1N NaOH and diluted with PBS so that the final concentration was 30 mg/ml. In those groups that received only the test compounds, a single dose (up to 1000 mg/kg) was given i.p. and any toxic deaths were autopsied and hematoxylin and eosin sections obtained. Surviving mice were observed for thirty days. In those groups receiving both test compound and cysteine, cysteine (1000 mg/kg) was given i.p. both 1 hour prior to and 2 or 3 hours after i.p. injection of the test compound. In Table 3 are the results of these experiments. The data indicated that the most toxic AA-CHP was Phe-CHP, followed by Leu-CHP and that Ala-CHP, Glu-CHP and Lys-CHP were non-toxic up to 1000 mg/kg. Furthermore, CHP-OEt had an $LD_{50}$ between 400–550 mg/kg and that Boc-Leu-CHP-BSA and Leu-CHP-BSA were non-toxic up to 2000 mg/kg.

toxicity with each other but a different pattern from that of Phe-CHP. Nine of nine animals receiving an i.p. injection of Leu-CHP (1000 mg/kg) and four of four animals receiving an i.p. injection of CHP-OEt in 7% DMSO (550 mg/kg) died within 8 hours of treatment. All animals showed moderate to severe pulmonary congestion and edema with an eosinophilic protein transudate present in some alveoli. While these histologic changes could be due to left heart failure caused by myocardial toxicity of the administered compounds careful light microscopic examination of the heart revealed no evidence of a toxic insult. In mice treated with Leu-CHP, one could also see early signs of ATN but these changes were not nearly as striking as in the case of Phe-CHP. None of the other AA-CHP's caused even a transient illness in any of the mice after intraperitoneal injection.

The MPD's (XVI and XVII) were non-toxic at doses up to 2000 mg/kg. This dose had to be injected in two doses of 1000 mg/kg each three hours apart since the maximum solubility of the MPD's in $H_2O$ at pH 7–8 was 30 mg/ml. Since these compounds are macromolecules and since it was expected that the cells of the reticulo endothelial system of the liver and spleen would ingest these compounds by pinocytosis, evidence of splenic toxicity was sought in 5 mice receiving 2000 mg/kg of Leu-CHP-BSA (XVII) i.p. and compared with that in 5 mice receiving 2000 mg/kg BSA i.p. The mice were sacrificed two days after injection and their spleens removed and weighed. There was no statistically significant difference between the two groups.

When 3 mice given a 600 mg/kg i.p. dose of Phe-CHP ($LD_{100}$) were pretreated 1 hour before with a 1000 mg/kg i.p. dose of cysteine and post-treated 3 hours after with 1000 mg/kg i.p. dose of cysteine, none of the cysteine-treated mice died while 6 of 7 given Phe-CHP died within 44 hours. When the same experiment was performed using Leu-CHP (1000 mg/kg i.p., $LD_{100}$) only one of three treated mice died and that was on Day 3, not within 8 hours as was typical of all 9 control mice. Histologic sections of the cysteine and Leu-CHP treated mouse that died on Day 3 showed no evidence

TABLE 3

Toxicity of AA—CHP's, CHP—OEt, and MPD's

| Compound | Dose ($\frac{mg}{kg}$) ($\frac{\text{number surviving}}{\text{number treated}}$) | $LD_{50}$ ($\frac{mg}{kg}$) | Pulmonary Congestion and Edema | Acute Renal Tubular Necrosis |
|---|---|---|---|---|
| Leu—CHP | 600(5/5),750(3/3),1000(0/9) | 750–1000 | ++–+++ | +–0 |
| Phe—CHP | 400(3/5),600(1/7) | 400 | 0–+ | +++ |
| Ala—CHP | 600(5/5),1000(6/6) | >1000 | | |
| Lys—CHP | 600(5/5),1000(6/6) | >1000 | | |
| Glu—CHP | 600(5/5),1000(6/6) | >1000 | | |
| CHP—OEt | 400(3/3),550(0/4) | 400–550 | +++ | 0 |
| XVI | 2000(6/6) | >2000 | | |
| XVII | 2000(6/6) | >2000 | | |

0 = absent
+ = mild
++ = moderate
+++ = severe

Phe-CHP was the most toxic of all the compounds tested and 6 of 7 animals receiving an i.p. dose of 600 mg/kg died within 36–44 hours after injection. Histologic examination of these animals revealed very consistent findings from animal to animal. Phe-CHP resulted in severe acute renal tubular coagulative necrosis (ATN). Pulmonary congestion and edema, as seen with Leu-CHP and CHP-OEt were minimal. Both Leu-CHP and CHP-OEt showed a similar histologic pattern of pulmonary congestion or edema.

From these data, summarized in Table 4, it is clear that cysteine was effective in protecting mice from the lethal toxicity of both Phe-CHP and Leu-CHP attesting to the sulfhydryl reactivity of the hydrolytic products of these two compounds.

The invention now being fully described, it will be apparent to one of ordinary skill in the art that many changes and modifications can be made thereto without departing from the spirit or scope of the invention as set forth herein.

TABLE 4

Effect of Cysteine on Toxicity of Phe—CHP and Leu—CHP

| Compound | Cysteine | Dose | Number died / Number treated | Time of Death |
|---|---|---|---|---|
| Leu—CHP | No | 1000 mg/kg | 9/9 | <8 hours |
| Leu—CHP | Yes[a] | 1000 mg/kg | 1/3 | Day 3 © |
| Phe—CHP | No | 600 mg/kg | 6/7 | 36–44 hours |
| Phe—CHP | Yes[b] | 600 mg/kg | 0/3 | |

[a]1 injection (1000 mg/kg) given 1 hour prior to treatment with Leu—CHP, 1 injection (1000 mg/kg) given 2 hours after treatment. All injections were given i.p.
[b]1 injection (1000 mg/kg) given 1 hour prior to treatment with Phe—CHP, 1 injection (1000 mg/kg) given 3 hours after treatment. All injections were given i.p.
© Autopsy H & E Sections showed no evidence of pulmonary congestion and edema.

What is claimed as new and intended to be covered by Letters Patent is:

1. Iminoquinone precursors having the formula:

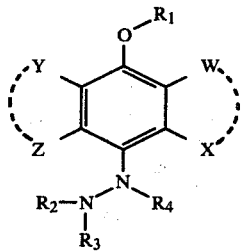

wherein (1) $R_1$ is hydrogen; phosphate; pyrophosphate; glycosyl; ribosyl; $C_1$–$C_{30}$ acyl or arylacyl wherein said acyl or arylacyl is attached to the remainder of said formula by a —CO— group; deoxyribosyl; aminoacyl having the formula —COCHR$_5$NH$_2$ where $R_5$ is selected from the group consisting of side chains present in naturally occurring amino acids; bovine serum albumin; or sulfate;

(2) $R_2$ and $R_3$ independently represent $R_1$, alkyl, aryl, or arylalkyl;

(3) $R_4$ is $R_2$, halogen, cyano, a radical of the formula

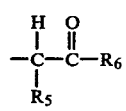

wherein (a) $R_5$ is selected from the group consisting of side chains present in naturally occurring amino acids and (b) $R_6$ represents hydroxy; alkoxy; —O$^-$M$^+$ where M$^+$ represents a singly charged metal ion; bovine serum albumin; or

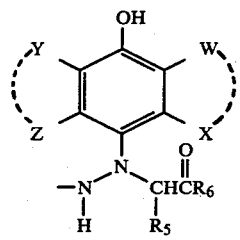

a radical of the formula

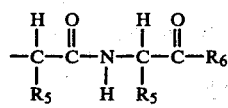

where
$R_5$ and $R_6$ have the meanings previously defined;

(4) O represents oxygen or —NH—; and (5) W, X, Y and Z independently represent hydrogen, halogen, hydroxy, alkoxy, aryloxy, alkylthio, amino, carboxyl, formyl, alkylamino, dialkylamino, acylamino, cyano, or nitro, or X and W or Y and Z taken together represents a carbocyclic ring having 5 to 6 ring atoms;

(6) with the provisos that at least one of $R_1$ or $R_2$ must be an enzymatically hydrolyzable phosphate, pyrophosphate, glycosyl, ribosyl, deoxyribosyl, acyl, arylacyl, aminoacyl, bovine serum albumin, or sulfate group and when $R_1$ is hydrogen, neither $R_3$ nor $R_4$ may inhibit the enzymatic hydrolysis of $R_2$.

2. The iminoquinone precursors of claim 1, wherein
$R_1$ is hydrogen;
$R_2$ is acyl, arylacyl, aminoacyl or phosphate;
$R_3$ is hydrogen; and
$R_4$ is —CHR$_5$COR$_6$.

3. The iminoquinone precursors of claim 2, wherein $R_2$ is aminoacyl.

4. The iminoquinone precursors of claim 3, wherein $R_2$ is

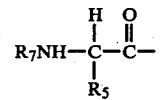

where $R_5$ is selected from the group consisting of side chains present in naturally occurring amino acids.

5. The iminoquinone precursors of claim 4, wherein $R_6$ represents hydroxy, alkoxy having 1–5 carbon atoms, or —O$^-$M$^+$ where M$^+$ represents a singly charged alkali metal ion.

6. The iminoquinone precursors of claim 5, wherein $R_5$ is hydrogen.

7. The iminoquinone precursors of claim 6, which is β-N-(L-leucyl)-α-N-(carboxymethyl ethyl ester)-p-hydroxyphenylhydrazine.

8. The iminoquinone precursors of claim 6, which is β-N-(L-phenylalanyl)-β-N-(carboxymethyl ethyl ester)-p-hydroxyphenylhydrazine.

9. The iminoquinone precursors of claim 6, which is β-N-(L-alanyl)-α-N-(carboxymethyl ethyl ester)-p-hydroxyphenylhydrazine.

10. The iminoquinone precursors of claim 6, which is β-N-(L-lysyl)-α-N-carboxymethyl ethyl ester)-p-hydroxyphenylhydrazine.

11. The iminoquinone precursors of claim 6, which is β-N-(L-glutamyl)-α-N-carboxymethyl ethyl ester)-p-hydroxyphenylhydrazine.

12. The iminoquinone precursors of claim 4, having the formula

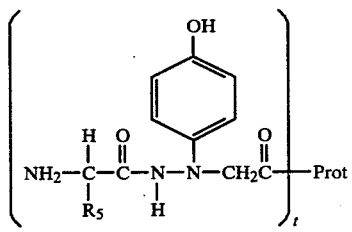

wherein Prot represents bovine serum albumin and t is from 1 to 500.

13. The iminoquinone precursors of claim 12, wherein Prot represent bovine serum albumin and t is from 1 to 120.

14. The iminoquinone precursors of claim 13, wherein $R_5$ is $(CH_3)_2CHCH_2-$.

15. A method of forming an iminoquinone in situ in a biological system, comprising administering a compound as described in claim 1, 2 or 4 to an organism.

16. The method of claim 15, wherein said organism is a unicellular organism or a yeast and said administering is by contact.

17. The method of claim 15, wherein said organism is a multi-cellular organism and administering is by contact, injection or ingestion.

18. The method of claim 17, wherein said iminoquinone is selectively formed in a first cell or tissue in the presence of a second cell or tissue in a multi-cellular organism.

19. The method of claim 15, wherein said administering is in the presence of a suitable pharmaceutical carrier.

20. The method of claim 17, wherein said administering is in the presence of a suitable pharmaceutical carrier.